United States Patent
Kassegne et al.

(10) Patent No.: US 11,877,851 B2
(45) Date of Patent: Jan. 23, 2024

(54) GLASSY CARBON PROBE AND MICROFABRICATION METHOD

(71) Applicant: San Diego State University Research Foundation, San Diego, CA (US)

(72) Inventors: Samuel K. Kassegne, San Diego, CA (US); Surabhi Nimbalkar, San Diego, CA (US); Arvind Balasubramani, San Diego, CA (US)

(73) Assignee: San Diego State University Research Foundation, San Diego, CA (US)

( * ) Notice: Subject to any disclaimer, the term of this patent is extended or adjusted under 35 U.S.C. 154(b) by 835 days.

(21) Appl. No.: 16/642,854

(22) PCT Filed: Aug. 30, 2018

(86) PCT No.: PCT/US2018/048938
§ 371 (c)(1),
(2) Date: Feb. 27, 2020

(87) PCT Pub. No.: WO2019/046631
PCT Pub. Date: Mar. 7, 2019

(65) Prior Publication Data
US 2021/0068696 A1    Mar. 11, 2021

Related U.S. Application Data

(60) Provisional application No. 62/552,304, filed on Aug. 30, 2017.

(51) Int. Cl.
*A61B 5/296* (2021.01)
*A61B 5/291* (2021.01)
(Continued)

(52) U.S. Cl.
CPC .............. *A61B 5/296* (2021.01); *A61B 5/291* (2021.01); *A61B 5/377* (2021.01); *A61N 1/0456* (2013.01);
(Continued)

(58) Field of Classification Search
CPC ........... A61B 5/25; A61B 5/263; A61B 5/293; A61B 5/294; A61B 5/296; A61N 1/0456; A61N 1/0476; A61N 1/0534
See application file for complete search history.

(56) References Cited

U.S. PATENT DOCUMENTS

| | | | |
|---|---|---|---|
| 8,147,486 B2 * | 4/2012 | Honour | A61N 1/05 606/41 |
| 2001/0000187 A1 | 4/2001 | Peckman | |

(Continued)

OTHER PUBLICATIONS

United States Patent and Trademark Office, International Search Report and Written Opinion for PCT/US18/48938 dated Nov. 14, 2018, 8 pages.

*Primary Examiner* — Eun Hwa Kim
(74) *Attorney, Agent, or Firm* — Mintz Levin Cohn Ferris Glovsky and Popeo, P.C.

(57) ABSTRACT

A probe device is disclosed that includes one or more insulating layers and a glassy carbon layer. The glassy carbon layer includes one or more channels. Each channel includes a microstructure, which may include an electrode region, interconnect region, and bump pad region. The electrode region may be placed in contact with a human or animal patient or test subject and used to collect or deliver signals in applications such as electrocorticography (ECoG), electromyography (EMG), and neural stimulation. A method of making a probe includes depositing a glassy carbon precursor on a substrate, patterning the precursor using photolithography, pyrolyzing the precursor to allow the (Continued)

formation of glassy carbon, and depositing one or more insulating layers.

13 Claims, 21 Drawing Sheets

(51) Int. Cl.
*A61B 5/377* (2021.01)
*A61N 1/04* (2006.01)
(52) U.S. Cl.
CPC ...... *A61N 1/0476* (2013.01); *A61B 2562/028* (2013.01); *A61B 2562/0285* (2013.01); *A61B 2562/04* (2013.01); *A61B 2562/125* (2013.01); *A61B 2562/16* (2013.01)

(56) References Cited

U.S. PATENT DOCUMENTS

| | | | |
|---|---|---|---|
| 2007/0239059 A1 | 10/2007 | McIver | |
| 2011/0125204 A1 | 5/2011 | Louise | |
| 2012/0255860 A1 | 10/2012 | Briman | |
| 2016/0073920 A1 | 3/2016 | Kassegne | |
| 2017/0028191 A1* | 2/2017 | Mercanzini | A61N 1/0534 |

* cited by examiner

GLASSY CARBON PROBE AND MICROFABRICATION METHOD

CROSS-REFERENCE TO RELATED APPLICATIONS

This application is a national stage filing of International Application No.: PCT/US2018/048938, filed Aug. 30, 2018, entitled "GLASSY CARBON PROBE AND MICROFABRICATION METHOD" which application claims priority to U.S. Provisional Patent Application 62/552,304, filed Aug. 30, 2017, the contents of which are herein incorporated by reference in their entirety.

STATEMENT OF GOVERNMENT SUPPORT

This invention was made with government support by the National Science Foundation (NSF) under Grant No. EEC-1028725. The U.S. Government has certain rights in the subject matter of the present disclosure.

TECHNICAL FIELD

The subject matter disclosed herein relates to probes and a fabrication process for creating glassy carbon probes.

BACKGROUND

A probe may be a device placed in contact with, for example, a patient, a test subject (e.g., a human or animal subject), and/or the like. Depending on the application, a probe may be referred to as a sensor, a transducer, an electrode, a microelectrode, or a transistor. An external probe may be placed in contact with a subject's tissue, such as the skin, and used for measurements, such as monitoring brain activity during electroencephalography (EEG) and/or the like. An external probe may also be used to deliver electrical impulses to a subject. For example, the external probe may be used to stimulate muscles during physical therapy, a technique known as transcutaneous electrical neuromuscular stimulation (TENS). A probe may be implantable inside the body of the subject. Examples of implantable probes include probes used in pacemakers to monitor and/or stimulate heart activity. When a probe is implanted for a very long period, such as, for example, months or years, it may be referred to as a chronically implanted probe.

One class of implantable probe is a neural probe, which may be placed in contact with the brain or spinal cord of the subject. When implanted, the probe may be used to detect electrical impulses to monitor activity in specific parts of the brain or spinal cord, including, for example, electrocorticography (ECoG) or electromyography (EMG.) Probes placed in contact with the brain or spinal cord may also be used to deliver electrical impulses to stimulate specific regions of the brain or spinal cord.

SUMMARY

In some example embodiments, there is provided a probe comprising a first insulating layer; and a glassy carbon layer on at least a portion of the first insulating layer, wherein the glassy carbon layer is composed of glassy carbon configured to provide one or more channels, wherein the one or more channels each includes a microstructure comprising a bump pad, an interconnect, and an electrode.

In some variations, one or more of the features disclosed herein including the following features can optionally be included in any feasible combination. The probe may further include a second insulating layer on at least a portion of the glassy carbon layer, the second layer is layered over the interconnect, wherein the second insulating layer is not layered over the bump pad and the electrode. The probe may include a plurality of channels and a corresponding plurality of microstructures configured in an array of electrodes. The bump pad may be configured as an interface to enable the probe to be coupled to at least an external. The microstructure may include the bump pad, the interconnect, and the electrode are composed of the same glassy carbon material. The microstructure including the bump pad, the interconnect, and the electrode may be formed from a same layer of precursor material during pyrolysis. The array of electrodes may be configured as a microarray. The electrode may be sized between 1 square nanometer and 1 square meter to enable the electrode to make contact with, for example, at least a portion of a neuron or at least a portion of an organ of a patient or test subject. A device may be coupled to the probe by delivering and/or receiving, via at least the microstructure, a signal to the probe. The device may be configured to provide electrocorticography, electroencephalography, neural stimulation, or electromyography. The glassy carbon may be formed from patterned pyrolysed carbon.

In some example embodiments, there is provided a method including depositing a glassy carbon precursor on a silicon wafer; patterning the glassy carbon precursor using photolithography; pyrolyzing the glassy carbon precursor to allow glassy carbon to form, wherein the glassy carbon comprises a glassy carbon layer, wherein the glassy carbon is configured to provides one or more channels, and wherein the one or more channels each includes a microstructure comprising a bump pad, an interconnect, and an electrode; and depositing a first insulating layer on the glassy carbon layer.

In some variations, one or more of the features disclosed herein including the following features can optionally be included in any feasible combination. The process may further include patterning the first insulating layer. The process may further include depositing a secondary substrate layer on top of the first insulating layer. The process may further include bonding a rigid substrate on the secondary substrate layer. The process may further include depositing a second insulating layer on the glassy carbon layer, wherein the second insulating layer is deposited on the glassy carbon layer on the opposite side from the first insulating layer; patterning the second insulating layer; and etching to remove the sacrificial transfer layer.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein.

DETAILED DESCRIPTION

Certain types of probes may be made by laminating component parts made from dissimilar materials, sometimes using adhesion layers. Some probes made in this fashion may be prone to failure due to delamination or a degradation of the adhesion. Depending on the materials used, some probes may fail due to a lack of tensile strength or due to repetitive stress and strain. Some probes have been found to cause tissue damage and/or trigger an immune response in patients or test subjects. Due in part to their size, some large probes can be difficult to place with a high degree of precision, which can lead to less accurate measurements, less accurate test results, and/or less effective therapies. Also due to in part to their size, large probes can also increase the likelihood of tissue damage and/or trigger an immune response in the patient or test subject.

In some example embodiments, there is provided a probe including a glassy carbon (GC) layer. Due in part to the biocompatibility of the glassy carbon material used, the probe may be implanted for a relatively long period of time with minimal tissue damage and minimal likelihood of triggering of an immune response, when compared to a probe not using the glassy carbon layer.

In some example embodiment, the probe may include no intermediate layers, such as an adhesion layer, a metal conductor layer, and/or the like, between a glassy carbon layer and one or more insulating layers. This lack of intermediate layers may reduce the likelihood of failures during long term use or implantation.

Figure 1A:
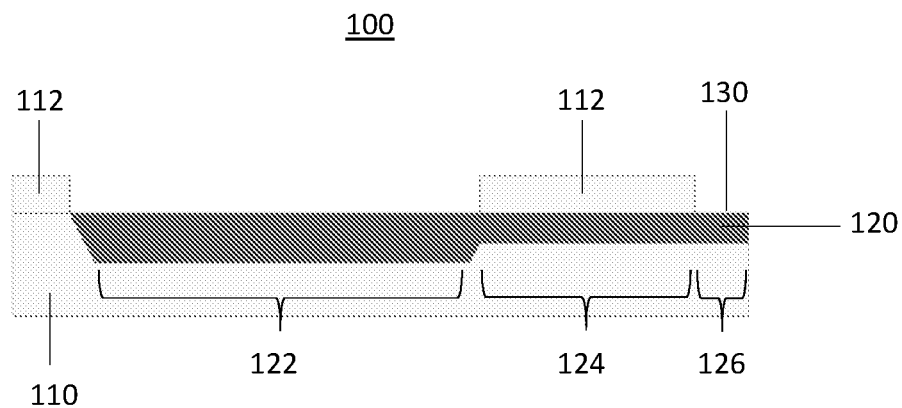
FIG. 1A depicts a side view of a probe.

FIG. 1A depicts a side view of a single channel probe 100, in accordance with some example embodiments.

The probe 100 may include a first insulating layer 110, a glassy carbon layer 120 covering at least a portion of the first insulating layer 110, and a second insulating layer 112 covering at least a portion of the glassy carbon 120 and first insulating layers 110.

According to some example embodiments, the glassy carbon layer 120 may include one or more channels. For example, as depicted in FIG. 1A, in a single channel probe the glassy carbon layer 120 may include one channel. As a further example, in a four channel probe, the glassy carbon layer may include four channels. The channels may be arranged in any configuration, depending on the application. For example, the channels may be arranged as an array, which may also be referred to as a microarray. According to some examples, a probe 120 including more than one channel may be referred to as a multi-channel probe.

Each channel in the glassy carbon layer 120 may include a microstructure including various regions. For example, a microstructure may include an electrode region 122, a trace or interconnect region 124, and a bump pad region 126, although each microstructure may include other regions as well. The electrode region 122 may also be referred to as a microelectrode. The interconnect region 124 (which may also be referred to as a trace) may be located between the electrode region 122 and the bump pad region 126. Depending on the application, the probe 100 may be any size and shape. For example, the probe 100 may be configured to have a thickness of about 30 μm, a width of about 3 mm, and a length of about 17 mm, although other dimensions may be implemented as well, depending on the application. The probe 100 may be used, for example, as an intracortical stimulation probe, an intracortical recording probe, an ECoG probe, a deep brain stimulation probe, and/or for any other type of application.

The insulating layers 110, 112 may be composed of a material that is flexible, electrically insulating, and/or biocompatible. The amount of flexibility may be dependent upon the application, such that the probe can couple to the surface, such as tissue, neurons, and/or the like. For example, materials used for the insulating layers 110, 112 may include polymers, including polyimide, polymers derived from polyamic acid, and polymers derived from chemical vapor deposition, and/or the like. Commercially available materials which may be used for the insulating layers 110, 112 may include, for example, Durimide 115a (commercially available from FujiFilm), and Parylene (commercially available from Specialty Coating Services.) The insulating layers 110, 112 may prevent portions of the glassy carbon layer 120 from coming into contact with the environment and may provide added strength to the probe 100. In an example implementation, the first insulating layer 110 may be configured to have a thickness of about 1 to 10 μm, although other thicknesses may be used as well.

The glassy carbon layer 120 of the probe 100 may consist of a glassy carbon material formed during pyrolysis from a glassy carbon precursor material. The glassy carbon precursor may be a material that is suitable for patterning, such as a material suitable for photolithography. For example, AZ-4620 (AZ Electronic Materials) is a material that may be used for positive photolithography while another material, SU-8 (Microchem), may be used for negative photolithography. SU-8 is used here as an example.

The glassy carbon material 120 may be flexible and have the electrical characteristics coupling electrical impulses between a subject and external device, such as an ECoG, neurostimulator device, and/or the like. The glassy carbon material may be considered biocompatible, reducing the likelihood of triggering an immune response in a subject.

At least a portion of the glassy carbon layer 120 (including the electrode region 122 of the microstructure) may be exposed to enable contact with, for example, the subject being measured, monitored, probed, and/or the like. For example, at least a portion of the electrode 122 may make contact with a subject's tissue (e.g., to make measurements, transfer electrical impulses, and/or the like).

The interconnect region 124 of the microstructure of the glassy carbon layer 120 may be located between the electrode region 122 and the bump pad region 124 of the glassy carbon layer 120. The interconnect region 124 may be sandwiched between insulating layer 110 and insulating layer 112. The interconnect region 124 may have a width of 180 μm and a length between 3 mm and 17 mm, although other dimensions may be implemented as well.

The bump pad region 126 may be on the insulating layer 110. At least one surface 130 of the bump pad region 126 may be exposed to the environment to enable coupling to other devices. When used in a circuit for example, a small quantity of solder or other adhesive (or bonding) material may be placed on the exposed surface 130 of the bump pad region 126 in order to make an electrical connection between the probe 100 and the circuit.

Figure 1B:
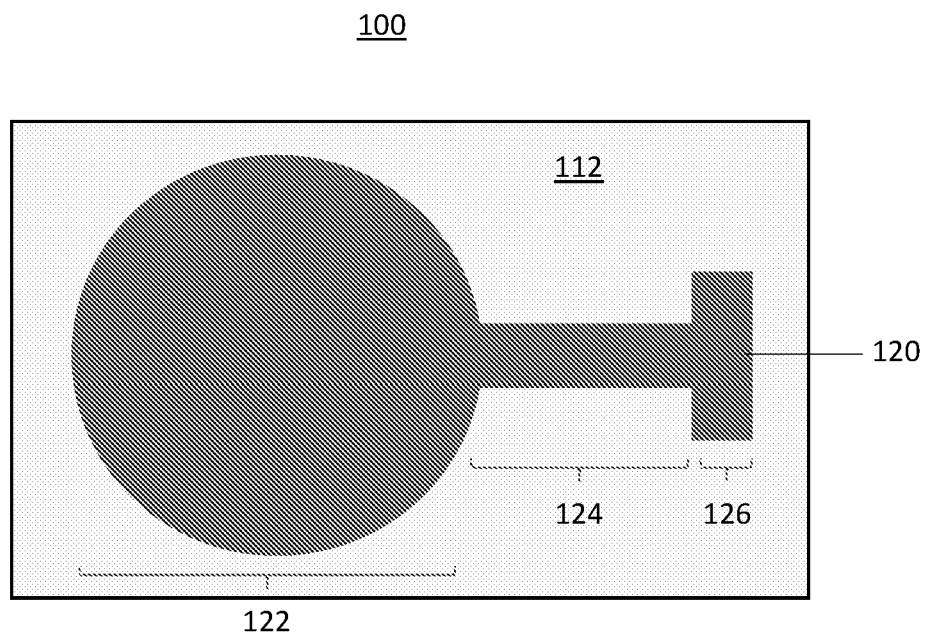
FIG. 1B depicts a top view of the probe of FIG. 1A.

FIG. 1B, depicts a top view of the probe 100. The insulating material used for the insulating layer 112 may opaque and/or transparent. In some cases, the insulating layer may be partially transparent, allowing the glassy carbon layer 120 to be seen through the insulating layers 110, 112.

Although the size and shape of the electrode region 122 of the glassy carbon layer 120 may vary based on the specific implementation, the electrode region 122 may be in the shape of a disc with a diameter of about 300 μm, although other sizes and/or shapes may be implemented as well. For example, the shape of the electrode region 122 may be a rectangle, triangle, a polygon, and/or an oval. In the case of the oval for example, the size may be about 20 μm and a length of about 25 μm. Depending on the application, according to some example embodiments, the electrode region may have a surface area between 1 square nanometer and 1 square meter, although other sizes may be used as well.

Figure 2:
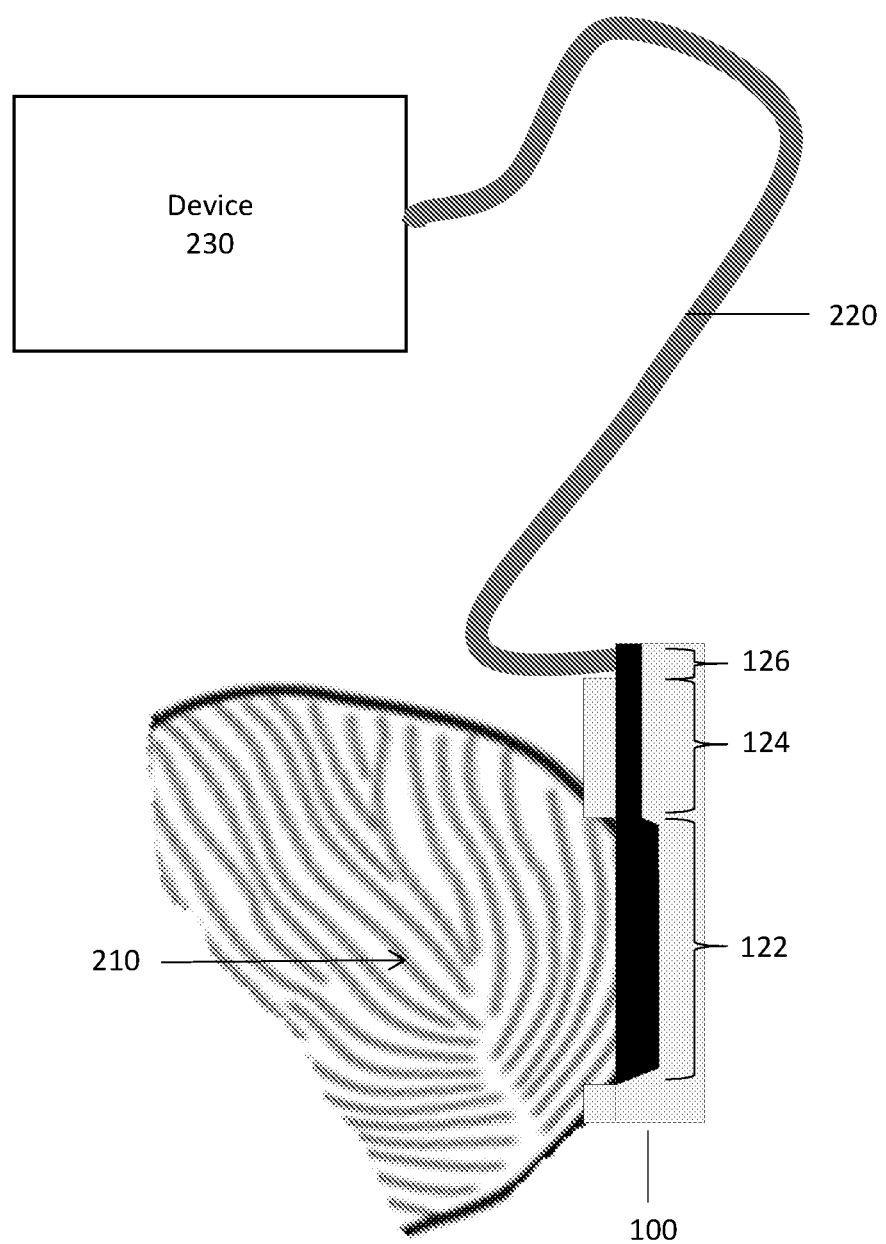
FIG. 2 depicts a circuit including the probe.

FIG. 2 depicts the probe 100 coupled to a device 230. For example, probe 100 may couple wirelessly and/or via wire 220 to the device 230. The device 230 may any type of device used for monitoring, measuring, and/or performing other operations. For example, the device 230 may be an electroencephalogram (EEG), a neural stimulator, and/or the like. In the example of FIG. 2, the wire 220 is connected to the probe 100 at the bump pad 126. The probe 100 may then be placed in contact with the subject 210. For example, the electrode region 122 may make contact with the subject's tissue 210. As noted, this contact may be external to the subject and/or internal to the subject. As shown, the device 230 may send and/or receive signals to the subject 210 via the wire 220, bump pad 126, trace 124, and electrode region 122.

Figure 3:
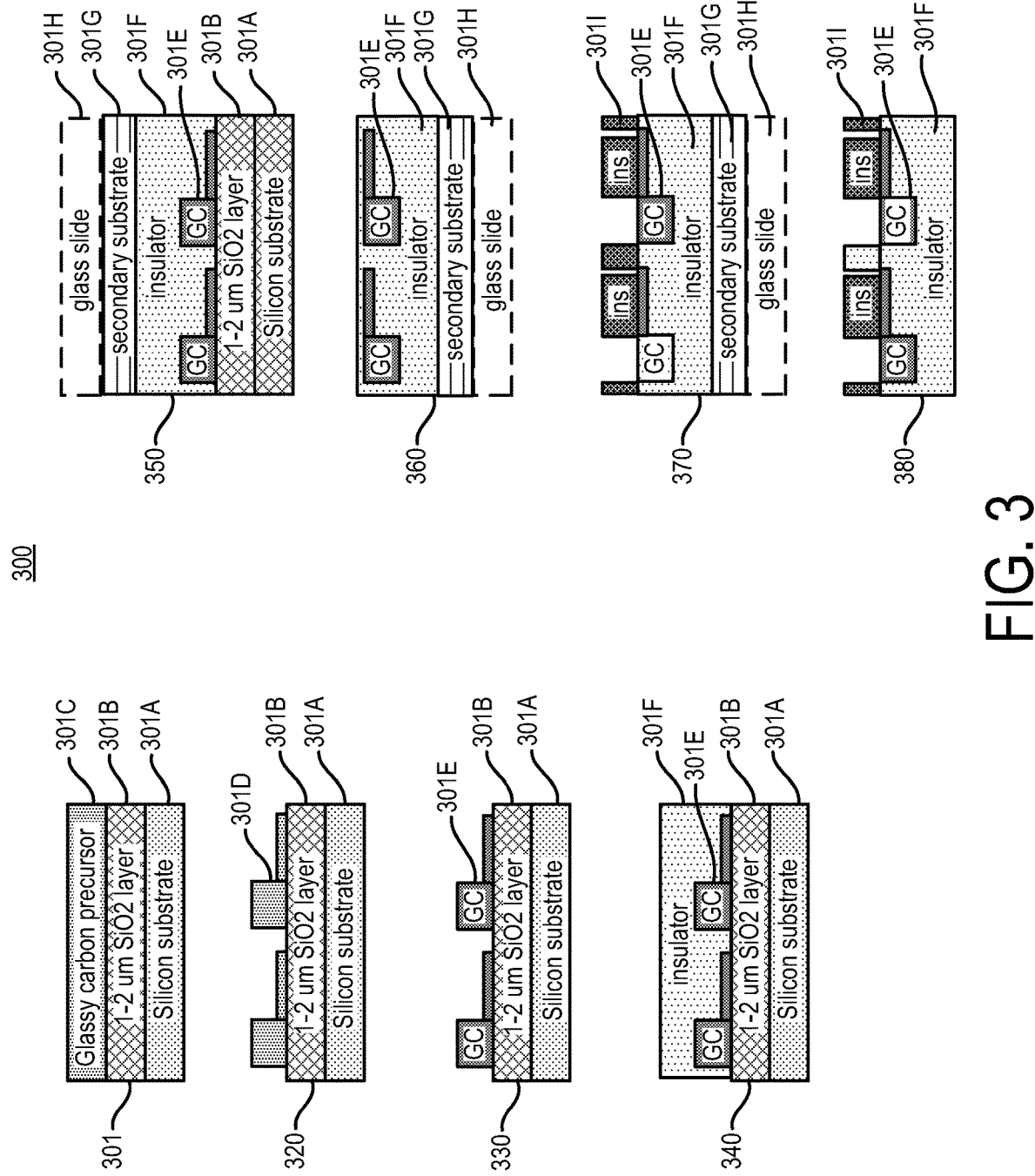
FIG. 3 depicts a process for fabricating a probe.

FIG. 3 depicts an example of glassy carbon probe microfabrication process 300 using, for example, chemical vapor deposition (CVD). The process 300 may include a two-step, double-sided pattern transfer process. In some example embodiments, the process 300 may include a pattern transfer process with no intermediate metal layers, allowing the probe's glassy carbon layer 120 to be composed of glassy carbon throughout including the electrode region 122, the interconnect region 124, and the bump pad region 126. The glassy carbon glassy layer 120 may be considered "homogeneous" in the sense that the glassy carbon composition is found throughout the carbon layer 120 including the electrode region 122, the interconnect region 124, and bump pad region 126.

At 310, there is shown three layers, a silicon wafer 301A, an $SiO_2$ layer 301B, and a glassy carbon precursor 301C. For example a glassy carbon precursor 301C suitable for photolithography, such as, for example, SU-8 may be deposited on an $SiO_2$ layer. The glassy carbon precursor 301C may be deposited by spin-coating at about 1000 RPM for about 60 seconds for a thickness of about 6 μm, although other thickness may be used as well. When the layers 301A-C are formed, the wafer may then be soft-baked at 65° C. for about 10 minutes and 95° C. for about 30 minutes.

After the glassy carbon precursor 301C has been soft baked, the glassy carbon precursor layer 301C may then be patterned using photolithography to form patterned glassy carbon precursor, as depicted at 320 at 301D. The glassy carbon precursor 301C can be patterned by, for example, exposing it to ultra-violet (UV) light at about 600 $mJ/cm^2$. After exposure, a post-exposure bake may be performed by heating the wafer to about 65° C. for about 1 minute and then to 95° C. for about 10 minutes. The glassy carbon precursor, for example, SU-8 may then be developed, for example, by immersion in an SU-8 developer for about 3 to 5 minutes, and cured at 150° C. for about 30 minutes.

After photolithography has been completed, pyrolysis may allow a glassy carbon to form, as shown at 301E at 330. Pyrolysis may be performed in, for example, an atmosphere of nitrogen gas with a flow rate of 50 ml/minute in a quartz furnace at 1000° C. for about 90 minutes after gradually ramping to temperature over a period of about 6 hours, and followed by cooling to room temperature over a period of several hours.

After the formation of the glassy carbon 301E, a first insulating layer may then be deposited as layer 301F at 340 using a flexible insulating material, such as, for example, Durimide 115a. This layer may be applied on top of the glassy carbon structures 301E by spinning at about 2500 RPM for about 45 seconds, for a thickness of about 8 μm, although other thicknesses may be implemented as well. The wafer may then be soft baked at about 135° C. for about 2.5 minutes and cooled to room temperature.

After the first insulating layer has been applied, the first insulating layer may optionally be patterned using, for example, dry reactive ion etching. The patterned first insulating layer may then be partially cured by heating the wafer at about 200° C. for about 30 minutes in a nitrogen atmosphere.

After the first insulating layer 301F has been deposited, and, if desired, patterned, a secondary substrate may be deposited, as depicted at 301G at 350. The secondary substrate 301G is used to provide temporary support and alignment after the silicon layer 301A and $SiO_2$ layers are removed later in the process. A polymer such as, for example, polymethyl methacrylate (PMMA) or polydimethylsiloxane (PDMS) (Dow Corning, USA) may be used for the secondary substrate 301G at 350. The use of PDMS is described here as one example, so others may be used as well. The secondary substrate 301G may be deposited by spin coating the substrate material, for example PDMS, on top of the first insulating layer 301F at 350. Using PDMS as an example, the PDMS may be mixed with a curing agent in a 10:1 proportion and spin-coated at about 300 rpm for 45 about seconds. The PDMS layer may then be cured at about 90° C. for about 30 minutes.

After the secondary substrate layer 301G has been deposited and cured, an optional rigid substrate may be added to provide additional support and alignment. This optional rigid substrate is shown at 301H at 350. The material used for the rigid substrate 301H at 350 may include any suitable rigid material, including, for example, glass.

After the secondary substrate 301G and optional rigid substrate 301H have been added, the silicon substrate 301A and $SiO_2$ layer 301B may be removed using a buffered hydrofluoric acid (BHF) etch, and the wafer may be flipped over. At 360 the inverted wafer is shown with the optional rigid substrated 301H at the bottom and the glassy carbon structures 301E at the top.

After inverting the wafer, a second insulating layer may be deposited. As with the first insulating layer 301F, the second insulating layer may be any suitable insulating material, including, for example, Durimide 115a. The second insulating layer may be deposited by spin coating, spinning at about 1000 RPM for about 20 seconds, and then spinning at about 3000 RPM for about 45 seconds. The wafer may then be soft-baked at about 135° C. for about 8 minutes, then cooled to room temperature, forming the second insulating layer as shown at 301I at 370.

After the second insulating layer 301I has been deposited, it can be patterned as described earlier, for example, by dry reactive ion etching. The patterned second insulating layer 301I can then be cured by heating the wafer at about 150° C. for about 90 minutes in a nitrogen atmosphere.

After the second insulating layer 301I has been patterned and cured, a buffered hydroflouoric acid (BHF) etch can be used to remove the secondary substrate layer 301G at 370 and, if present, the rigid substrate 301H at 370.

FIG. 3 at 380 depicts the finished probe 100, with an first insulating layer 301F, a homogeneous glassy carbon layer 301E, and a second insulating layer 301I.

With respect to the first insulating layer 301F and the second insulating layer 301I, a non-photo sensitive polyimide (e.g., Durimide 115) may be used to provide better adhesion to the secondary substrate layer 301G, when compared to a photosensitive polyimide such as Durimide 4100.

Testing Methods

Mechanical and Cross-Sectional Characterizations. The mechanical strength of sample probes were measured using an Instron 1500HDX Universal Testing Machine (Instron, USA), where tensile load may be applied until failure, and the resulting extension measured. Probes with dimensions of 17 mm in length, 0.5 mm in width and 50 mm in thickness were used for the tests mechanical strength tests. Attachment of strain gauge extensometers directly to the probes was not practical because the devices were too thin. Instead, linear displacement due to the crosshead motion of Instron was used to obtain displacement values. Thread-rolled C-clamps with clamping capacity of 0-25 mm were used to grip the probes. The frame of C-clamps was then held between the jaws of the upper and lower clamps of the Instron machine. The cross-head extension rate was set to 0.5 mm/min. The probe was then loaded to failure at this rate and the load-deflection curve plotted. For comparison purposes, sample probes of similar geometry were used consisting of 200 nm thick metal (Pt) electrodes and wire traces, microfabricated through a standard metal lift-off process. Subsequently, the load-deflection curves and ultimate load carrying capacity of the thin-film metal probes were determined in a similar fashion. Young's Modulus was determined by taking the mean slope of ten points in the elastic region of the stress-strain curve. The modulus of plain Durimide insulating layer with no metal or glassy carbon traces and electrodes was also determined separately to de-couple its effect from the composite structure.

An FEI Quanta 450 FEG SEM (ThermoScientific, OR) was used for scanning electron microscopy images. Cross sectioning was obtained through focused ion beam (FIB) milling using a dual beam microscope system (Nova 600 NanoLab; FEI, Netherlands). This system was equipped with a field emission gun for scanning electron imaging and a focused ion beam of gallium ions for milling. The sectioning process was done in two steps: ion current milling (working at 30 kV and 7.7 pA) followed by a cleaning step of the section. Imaging was done at an acceleration voltage of 20 kV (0.4 nA of emission current).

Electrical, Electrochemical, and Stability Characterizations.

The electrochemical behavior of the electrodes was studied in phosphate-buffered saline solution (PBS; 0.01 M, pH 7.4; Sigma Aldrich, USA). Cyclic voltammetry (CV) was used to quantify capacitive charging and electrode stability while electrochemical impedance spectroscopy (EIS) was used to determine the electrical properties of the sample probes over a large range of frequencies. In both CV and EIS tests, potentiostat (Reference 600+, Gamry Instruments, USA) was connected to a three-electrode electrochemical cell with a platinum wire as a counter electrode and a saturated Ag/AgCl reference electrode. During CV tests, the working electrode potential was swept between 1.3 V and −0.9 V (water window of glassy carbon), maintaining a scan rate of 100 mV/s. The total charge storage capacity (CSC) was calculated from the time integral of a CV cycle. During EIS measurements, 10 mV RMS amplitude sine wave was superimposed on a 0 V potential with frequency sweep from 0.1 to $10^5$ Hz. Equivalent circuit modeling of the EIS data was done through Gamry Echem Analyst Vn 7.05 software (Gamry Instruments, USA). For accelerated aging tests, including prolonged current stimulation pattern tests, cathodic-first charge balanced bi-phasic current pulses were used with 450 µA amplitude, 400 msec cathodic half-phase period and a frequency of 1 kHz in a saline solution (0.01 M PBS) using a Gamry Instruments Virtual Front Panel (Gamry Instruments, PA, USA). This accelerated aging test corresponds to charge density of 0.25 $mC/cm^2$ and was applied over a period of 1000 hours. Voltage transient responses during stimulation were acquired using the same potentiostat (for example, PARSTAT 2273, available from Princeton Applied Research, USA) by simultaneously injecting stimulation current pulses and recording the corresponding voltage excursions between working and counter electrodes. In regular intervals, impedance was measured and the integrity of the electrodes checked. The buffer pH was measured regularly during accelerated aging test using pH/mv/ion benchtop meter (Jenco Electronics, TX).

Fast-Scan Cyclic Voltammetry (FSCV) was used to evaluate the electrodes' dopamine detection performance with a WaveNeuro Potentiostat System (Pine Research, NC). For in-vitro dopamine calibration, the FSCV waveform was used with a pyramidal excursion from −0.5 V to +1.3 V potential and back to baseline with respect to the Ag/AgCl reference electrode at a scan rate of 400 V/s and 10 Hz frequency. The duration of each scan was 9 ms (900 data points). Prior to the beginning of each experiment, the same voltage waveform was applied to the electrodes at 60 Hz for 1 hour for activating the carbon surface of the electrodes. Known concentrations of dopamine (10 nM-1 mM) were then infused over 5 seconds while changes in current were recorded for 20 seconds.

In-Vivo Tests.

Micro-ECoG Implantation.

All animal experiments were performed in accordance with the Association for Assessment and Accreditation of Laboratory Animal Care (AAALAC) Guide for the Care and Use of Laboratory Animals (8th Edition) and approved by the University of Washington Institutional Animal Care and Use Committee (IACUC) under protocol number 4265-01. Adult female Long-Evans rats (300 g) were used in this study and anesthesia was induced with a mixture of ketamine and xylazine. The animal was placed in a stereotaxic frame and a craniotomy made 1.5 mm rostral and 4.5 mm caudal to the bregma and 1 mm lateral and 7 mm lateral to the midline, targeting the left forelimb sensorimotor cortex. A probe, as described herein, was then placed on the dura and stabilized by gel foam dental cement. A reference wire was connected to a screw on the right parietal bone while a ground wire was connected to a screw on the occipital bone. Throughout the entire procedure, body temperature of the animal was maintained with a heating pad placed under it.

Electrophysiology Recording.

Brain signal recording sessions were carried out under anesthesia, 4 days after array implantation. An implanted aCG probe configured as an ECoG microarray was connected to a multichannel data acquisition system (Tucker-Davis Technologies, FL) through an active (unity-gain) head-stage. Sensory evoked potentials (SEPs) were obtained by applying bipolar surface stimulation to the surface of skin of the right wrist of an anesthetized rat. Recorded data was digitized at 24.4 kHz and stored on a PC for further analysis. Subsequently, raw signals were bandpass filtered (1-450 Hz, 4th order Butterworth, zero-phase) and down-sampled to 1 kHz using Matlab software (Mathworks, Inc., MA). Low-frequency brain activity in evoked SEPs were eliminated by a high-pass filter (30 Hz, 4th order Butterworth, zero-phase). In each recording session, 15 single, bi-phasic, squared wave stimulation pulses (pulse width: 500 µs, pulse amplitude: 0.5 mA-2 mA, 0.5 Hz) were applied to the surface electrodes and evoked response from 5 ms to 55 ms after stimulation onset were averaged to obtain average SEPs. The extracted evoked response between 5 ms to 55 ms after stimulation onset was considered as an estimate for the signal, while the extracted spontaneous activity corresponding to 65 ms to 115 ms after stimulation onset was taken as an estimate for the background noise. Subsequently, SNR (signal-to-noise ratio) of ECoG electrodes placed in six different positions across forelimb sensory cortex were evaluated. The SNR value for each trial was defined as the ratio between the variance of selected signal (evoked response) and the variance of selected noise (spontaneous activity). The calculated SNR (mean±standard deviation) of all channels was used as a useful indication of the quality of brain-signal recording. Furthermore, to show temporal-spectral representation of recorded data by glassy carbon electrodes, the spectrogram of each ECoG channel were computed by applying 256 ms Hanning window on each ECoG time-series. The corresponding short-time Fourier transform of each segment was then computed using 200 ms overlap.

Test Results

Extensive in-vivo and in-vitro mechanical, electrical, and electrochemical characterizations coupled with long-term stability and corrosion tests under electrical stimulations have been carried out using probes as described herein. These tests demonstrate robustness and multi-modal recording capability for both neuronal electrical signals and neurotransmitter electrochemical signals. These probes have been shown to be capable of delivering balanced-charge pulsing of over 3.5 billion cycles during an extended accelerated aging process lasting more than 1000 hours. Test further show that these probes represent an improvement over existing technologies in key metrics including, for example, mechanical, electrical properties, electrochemical kinetics, and sensitivity.

Figure 4:
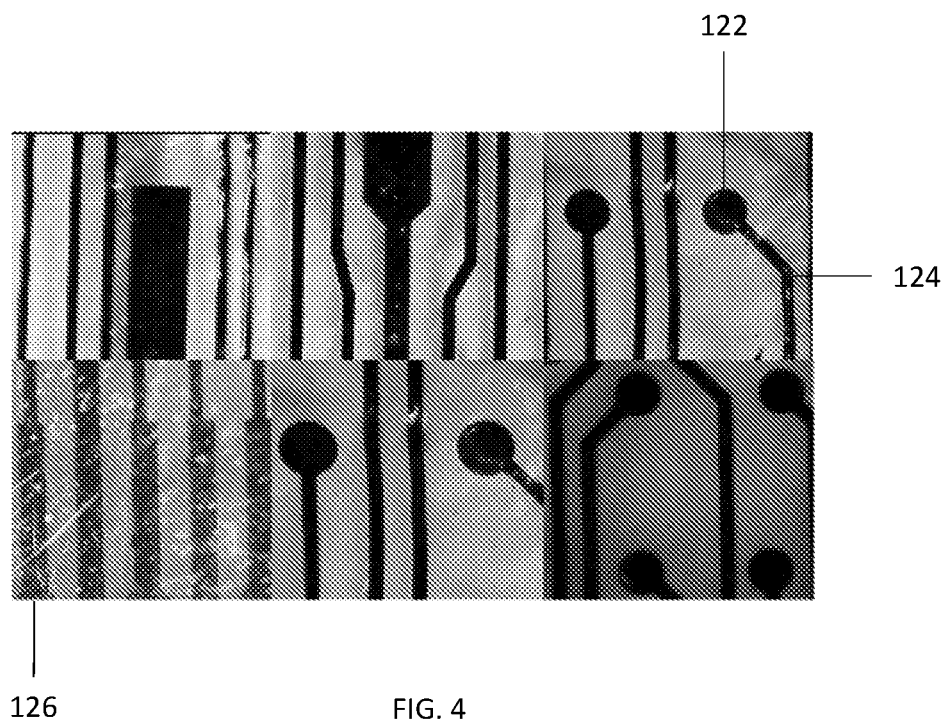
FIG. 4 depicts pictures of a probe.

FIG. 4 shows pictures, such as optical microscopy, of the probe, in accordance with some example embodiments. The electrode region 122, interconnect region 124 (visible through a transparent second insulating layer), and bump pad 126 are labeled.

Figure 5:
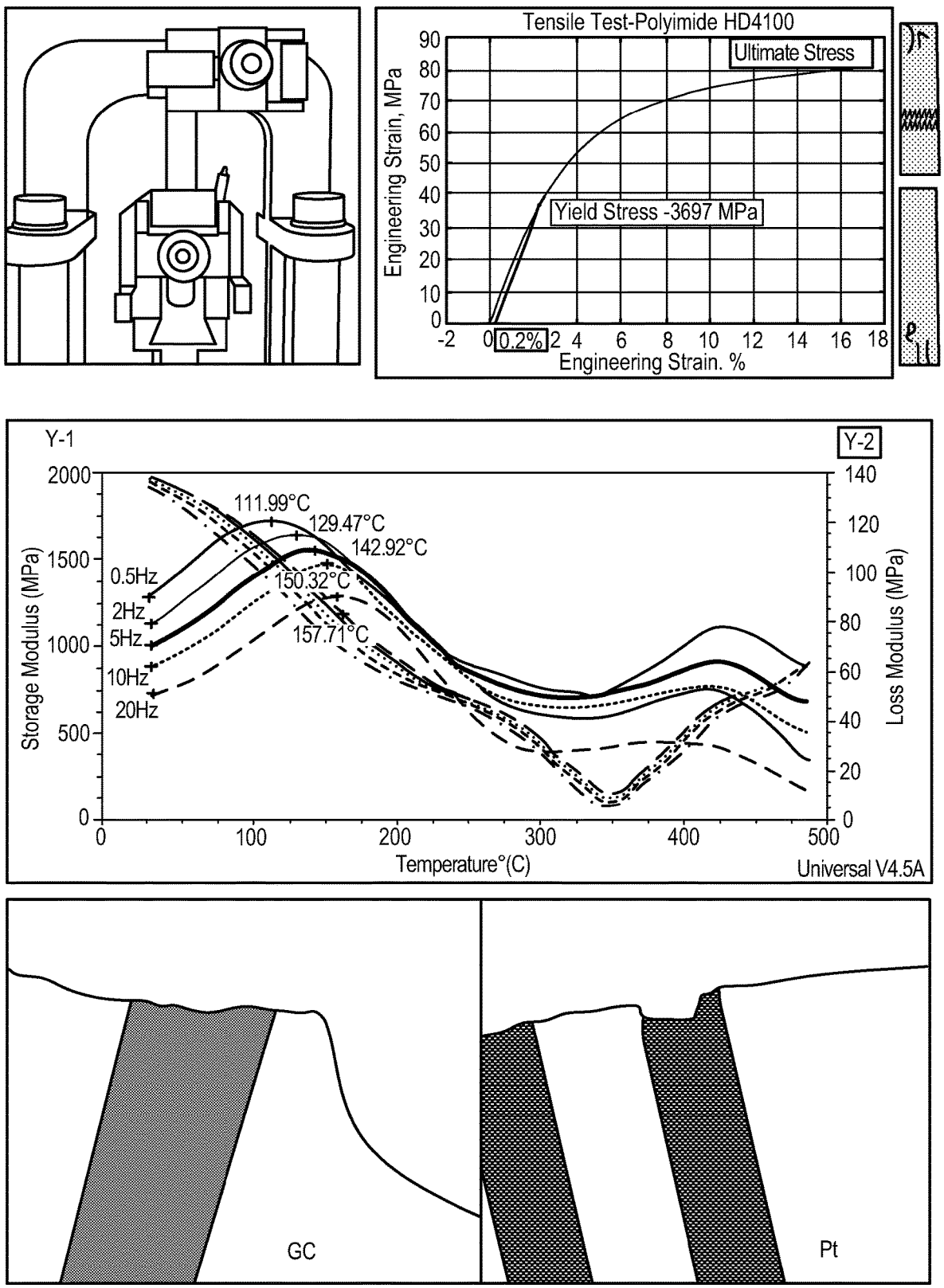
FIG. 5 depicts examples of the results of mechanical characterization testing of a probe.
Figure 6:
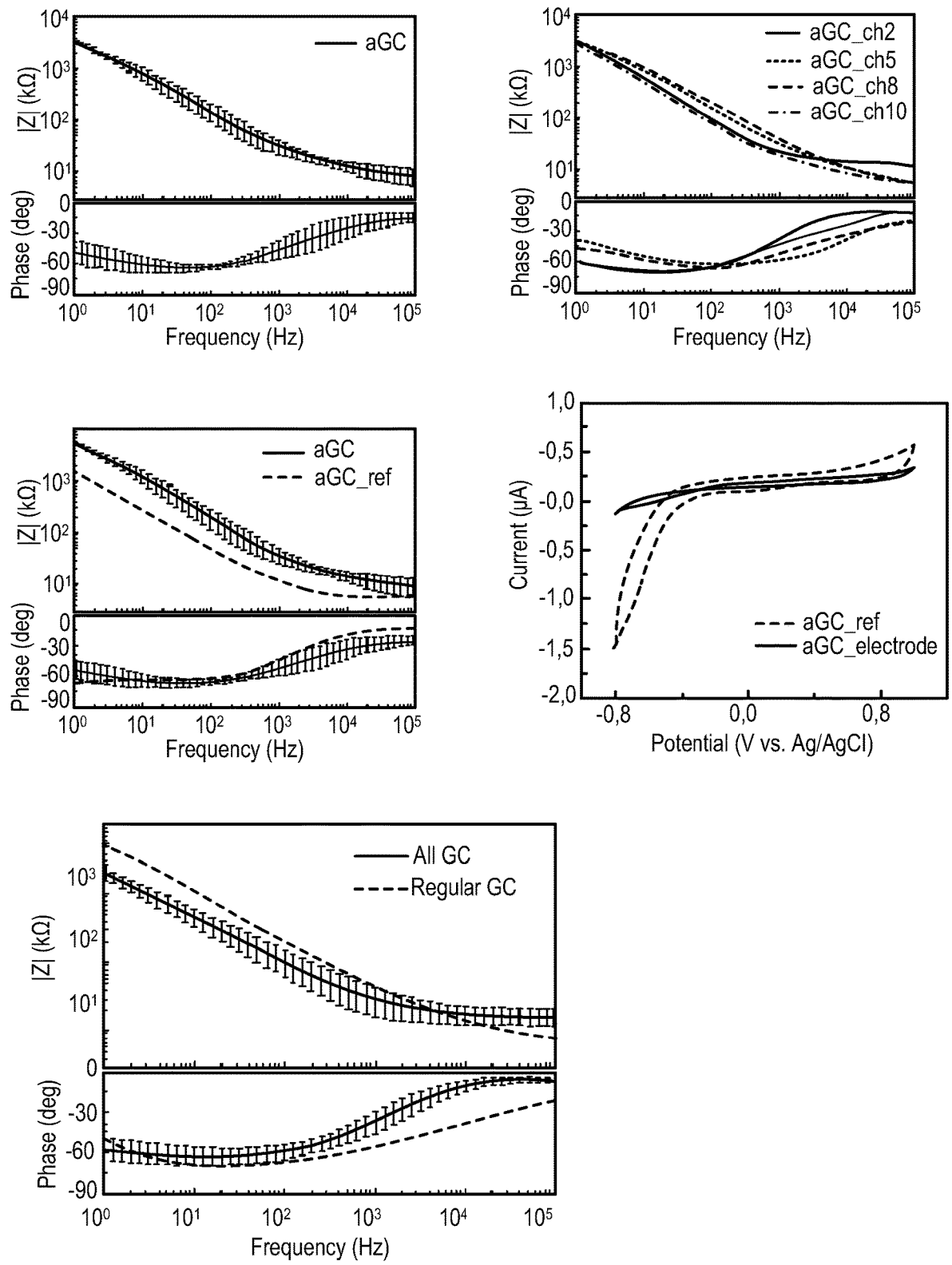
FIG. 6 depicts examples of the results of electrical characterization testing of a probe.

FIG. 5 depicts example results from mechanical characterization, including a stress-strain curve under a tensile load, failure plane at maximum load carrying capacity, and storage modulus as a function of temperature. Electrical characterization results are also provided at FIG. 6. FIG. 6 shows an average impedance of about 20 kΩ at a frequency of 1 KHz. A comparison is made with a previous generation of hybrid probe where a metal/glassy carbon interface is used. The impedance of probes, as described herein, is shown to be lower, potentially indicating that the contact resistance at the metal/glassy carbon interface of the metal/glassy carbon probe may have contributed to the increased impedance. This may highlight at least one advantage of using a homogeneous glassy carbon material in a probe.

Figure 7:
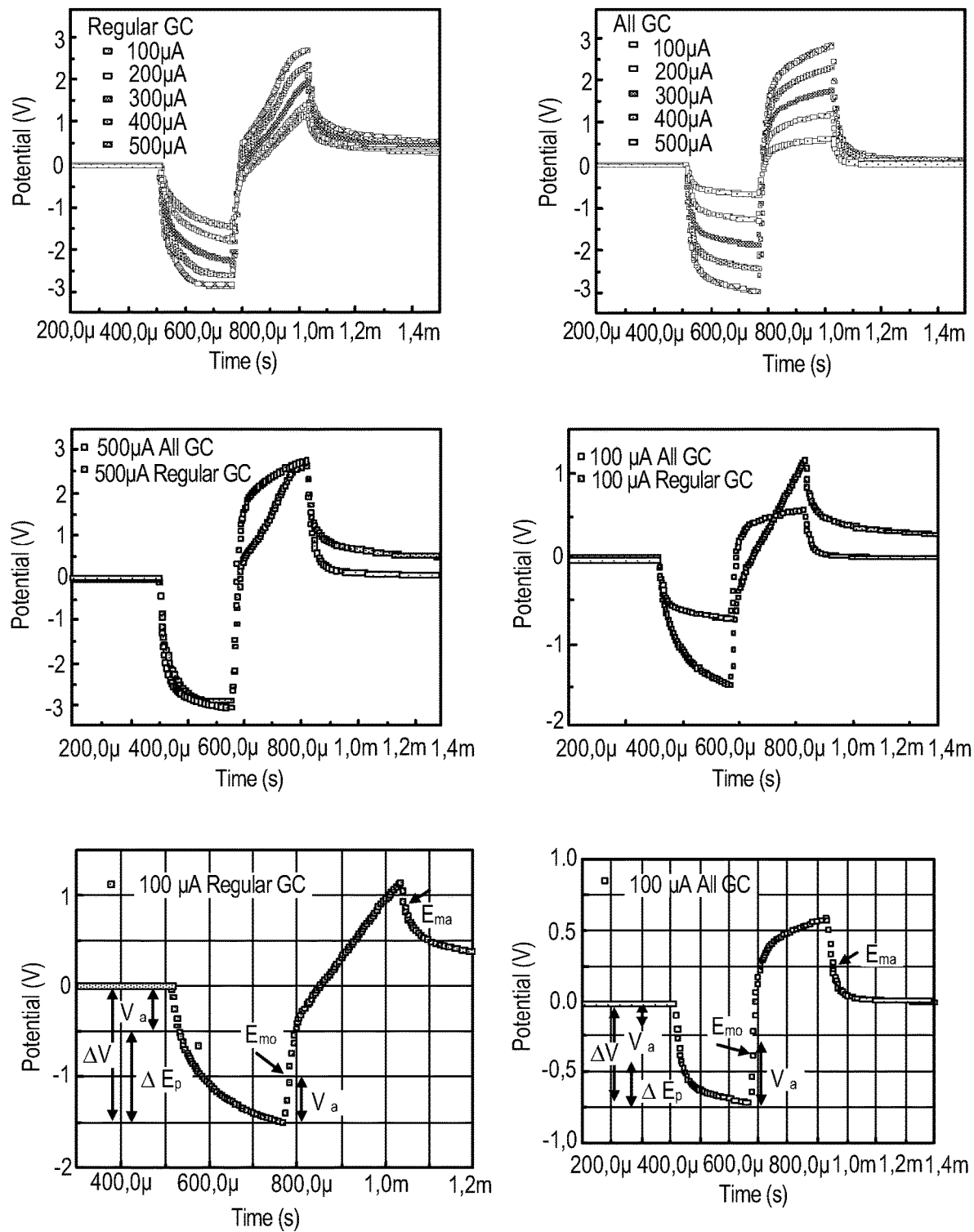
FIG. 7 depicts examples of results of electrical characteristics of a probe.

FIG. 7 shows electrical characteristics of example probes implemented according to example embodiments, demonstrating the electrochemical responsiveness of the example probes.

Figure 8:
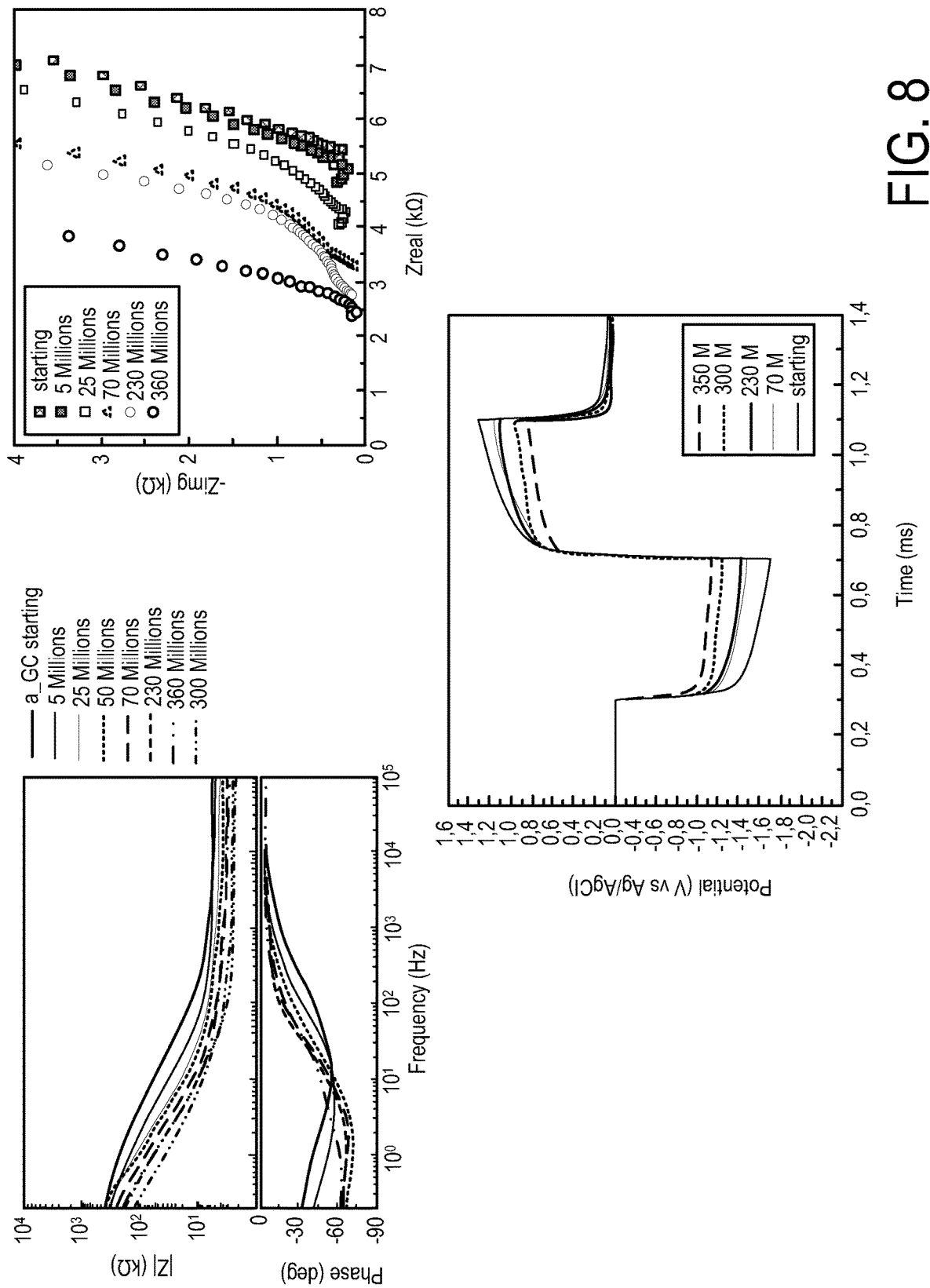
FIG. 8 depicts examples of results of bi-phasic pulse testing of a probe.

FIG. 8 shows the effects of bi-phasic pulsing on example probes implemented according to example embodiments, demonstrating the electrical stability of the example probes, including resistance to degradation.

Figure 9:
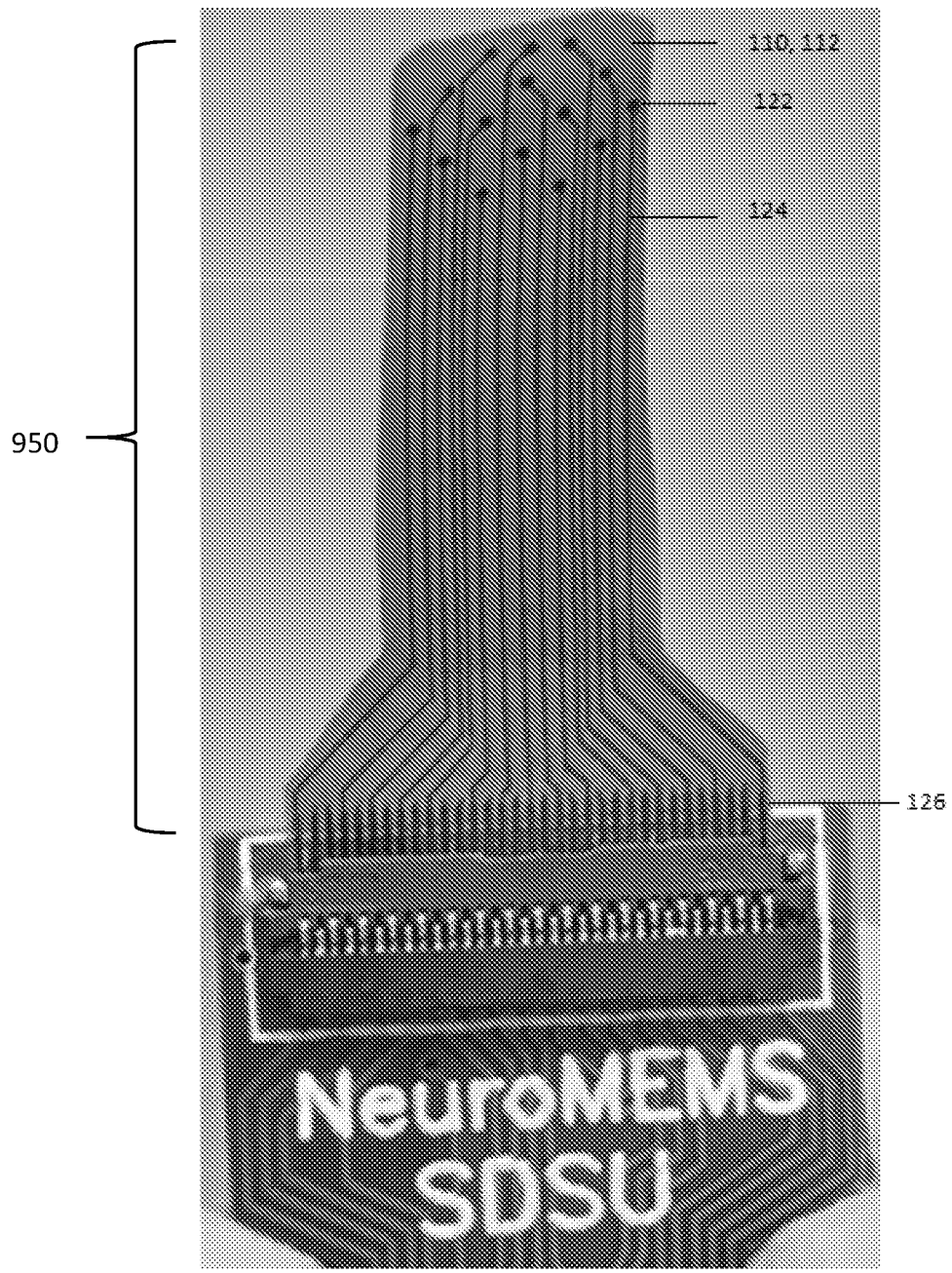
FIG. 9 depicts a picture of a 15-channel probe.

FIG. 9 depicts a multi-channel probe 950 including a glassy carbon layer, in accordance with some example embodiments. In the example of FIG. 9, the glassy carbon layer is used to provide 15-channels, each with a glassy carbon layer including a electrode 122, interconnect 124, and bump pad 126 regions. The insulating layers 110 and 112 are also visible. In the example of FIG. 9, the electrode region 122 has a size diameter of about 300 µm and the interconnect region 124 has a width of about 180 µm, although other sizes are possible. In the example, the total width of the probe 950 is about 3.5 mm. Zero insertion force (ZIF) connectors may be used to connect the probe 950 to a printed circuit board, which may be connected to a device, such as a multi-channel data acquisition system. This example probe 950 at FIG. 9 may be suitable for acquisition of electrocorticography (ECoG) readings, as well as other types of readings.

Figure 10:
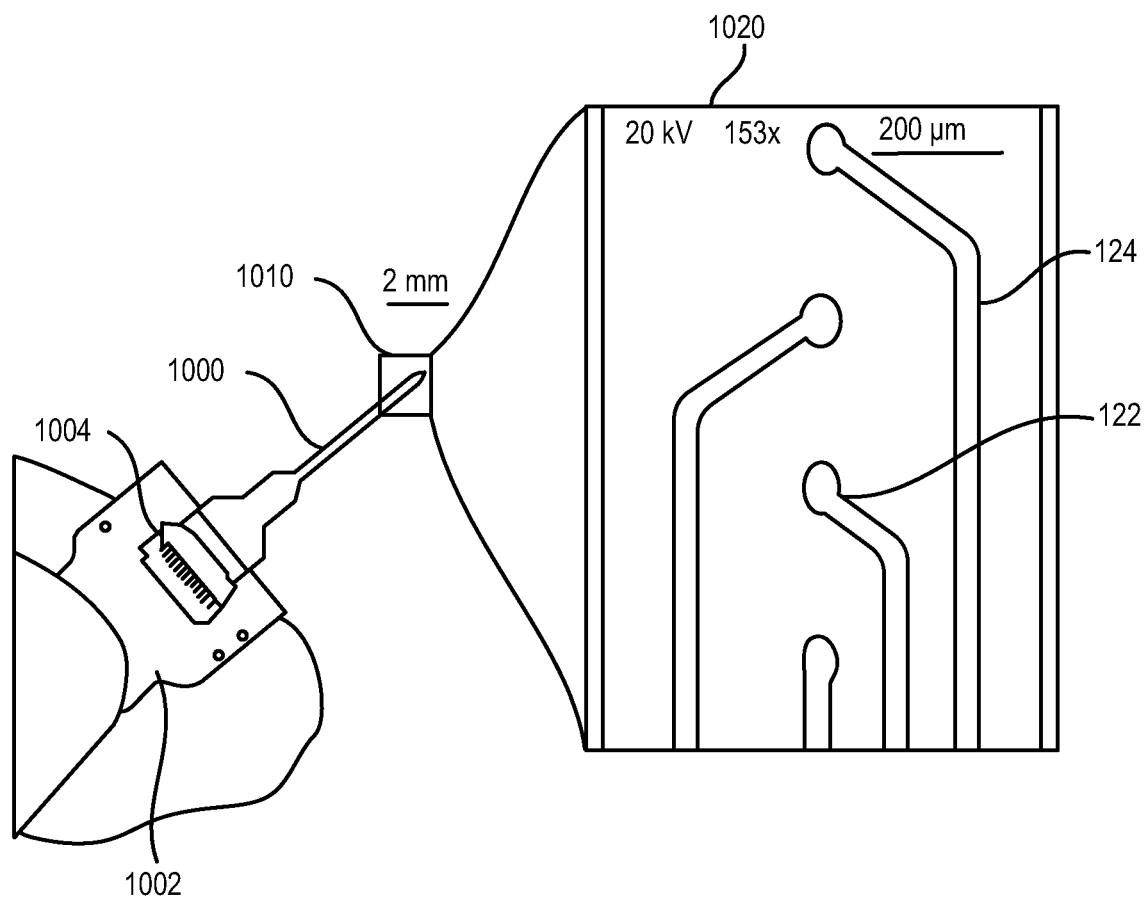
FIG. 10 depicts a 4-channel probe.

FIG. 10 depicts an example implementation of a 4-channel penetrating probe 1000. In the example of FIG. 10, the probe 1000 was used as an intercortical probe to detect dopamine levels, although the probe may be used in other applications. FIG. 10 shows the probe 1000 mounted on a printed circuit board 1002 using a zero insertion force connector 1004. FIG. 10 at 1020 shows a scanning electron microscope image of the probe 1000, showing four glassy carbon electrodes 122, each with exposed area of about 25 µm×20 µm (500 µm$^2$), spaced at about 220 µm. FIG. 10 at 1020 also shows the interconnect regions 124 of the probe. The width of the probe 1000 near the electrodes 122 is about 500 µm. The length of the probe is about 17 mm. Other shapes and dimensions may be implemented depending on the application.

Figure 11:
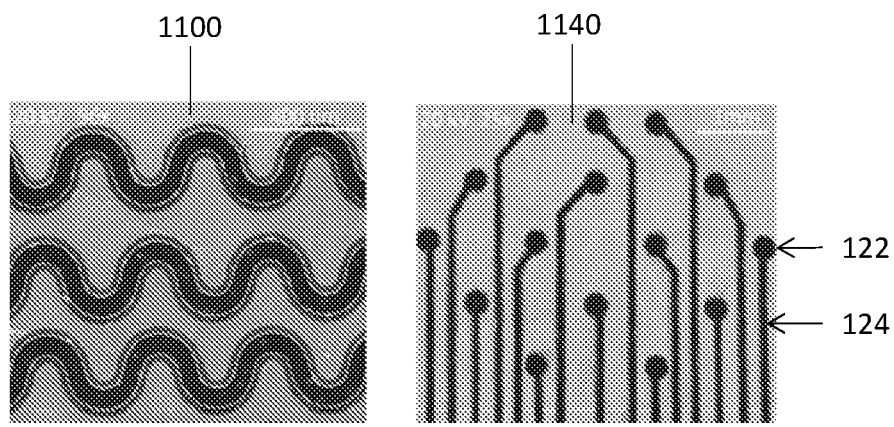
FIG. 11 depicts a picture of a 15-channel probe.

FIG. 11 depicts scanning electron microscope imaging after pyrolyzing a SU-8 photopolymer, which may be used as a precursor to form glassy carbon traces and electrodes as described herein. FIG. 11 at 1100 depicts serpentine-shaped glassy carbon traces, while FIG. 11 at 1140 depicts a close-up view of glassy carbon traces 124 and glassy carbon electrodes 122 with a diameter of about 300 μm.

Figure 12:
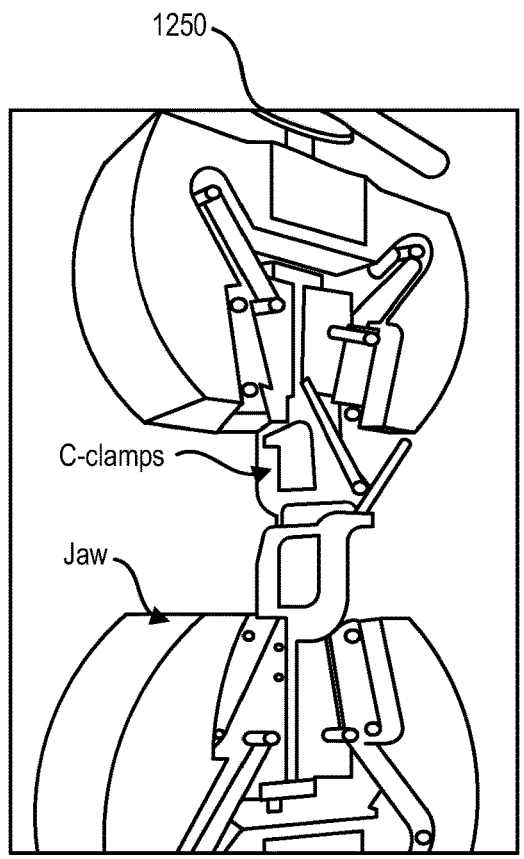
FIG. 12 depicts examples of the results of mechanical testing of a probe.
Figure 12:
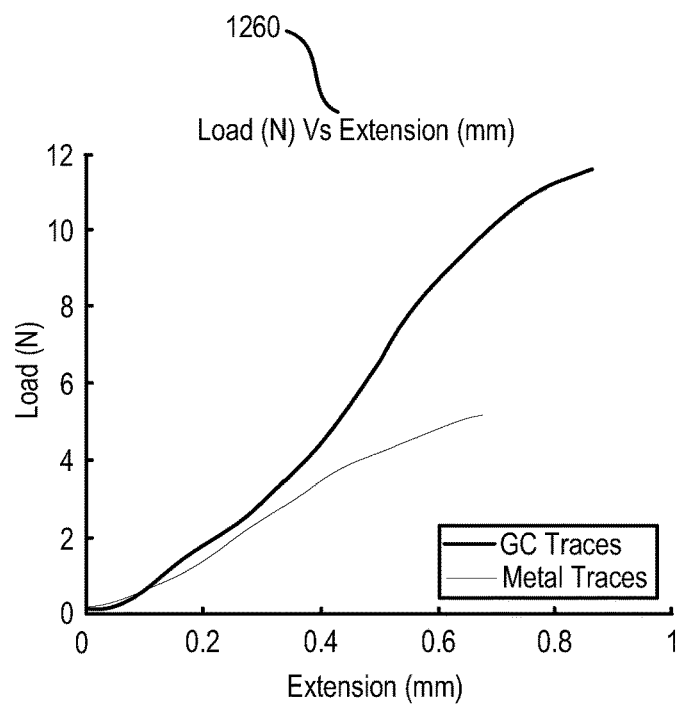

FIG. 12 at 1250 depicts the experimental setup of the Instron Universal Testing Machine for axial tensile loading of sample probes. FIG. 12 at 1260 depicts a comparison of load-deflection curve of probes as described herein versus with that of thin-film metal probes of similar geometry. The specimen probes used have a length of 17 mm, width of 3 mm, and thickness of 50 μm. As shown at 1260, the probe described herein may be able to withstand much greater loads than the thin-film metal probes tested.

Figure 13:
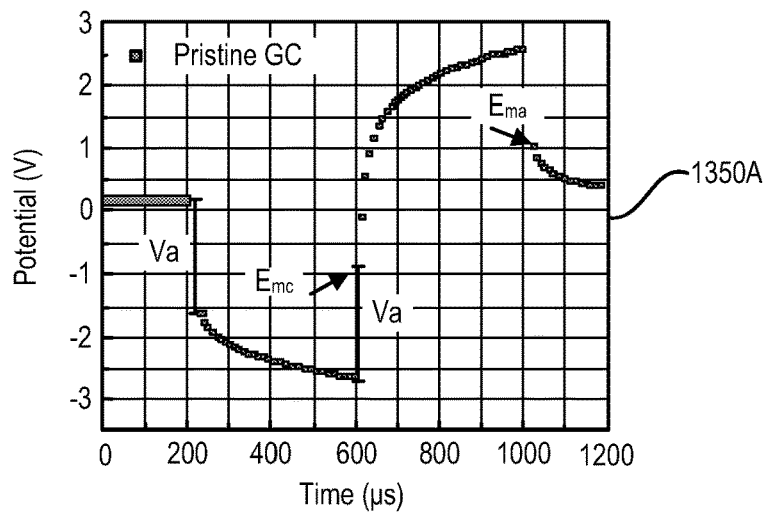
FIG. 13 depicts examples of the results of electrical testing of a probe.
Figure 13:
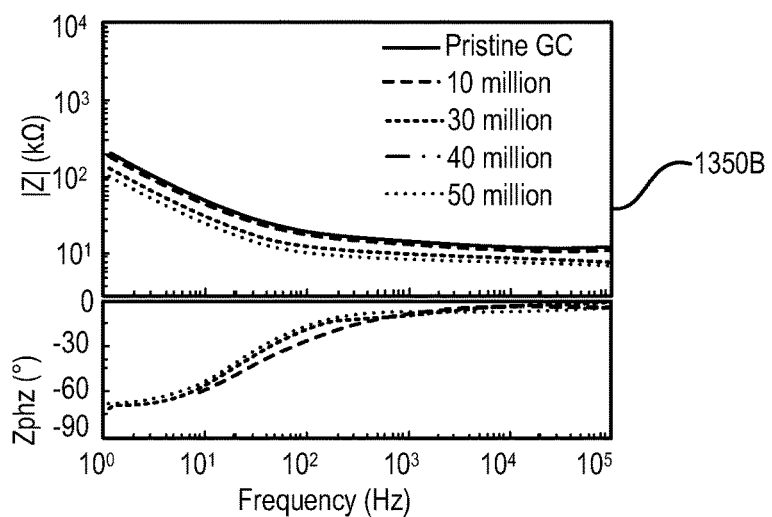
Figure 13:
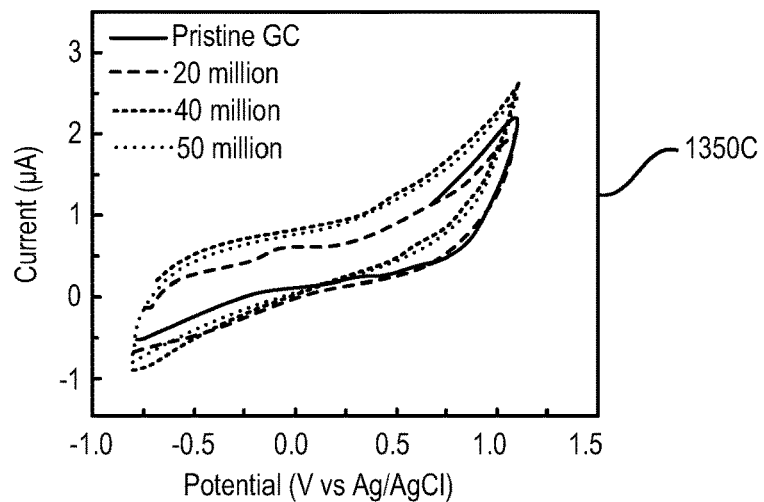

FIG. 13 depicts a plot 1350A of voltage transients of glassy carbon electrodes in response to a 5.2 mA biphasic pulse corresponding to 3 mC/cm$^2$ charge density. FIG. 13 at 1350B depicts the impedance spectra of glassy carbon electrodes before and after 10, 30, 40, and 50 million cycles of 3 mC/cm$^2$ stimulation pulses in phosphate buffered saline (PBS.) As shown here, very little change in the impedance characteristics of the probes were observed after many millions of test cycles. FIG. 13 at 1350C depicts the corresponding cyclic voltammograms. $Q_{inj}$ is calculated as the time integral of current in the loading phase normalized by the geometric area.

Figure 14:
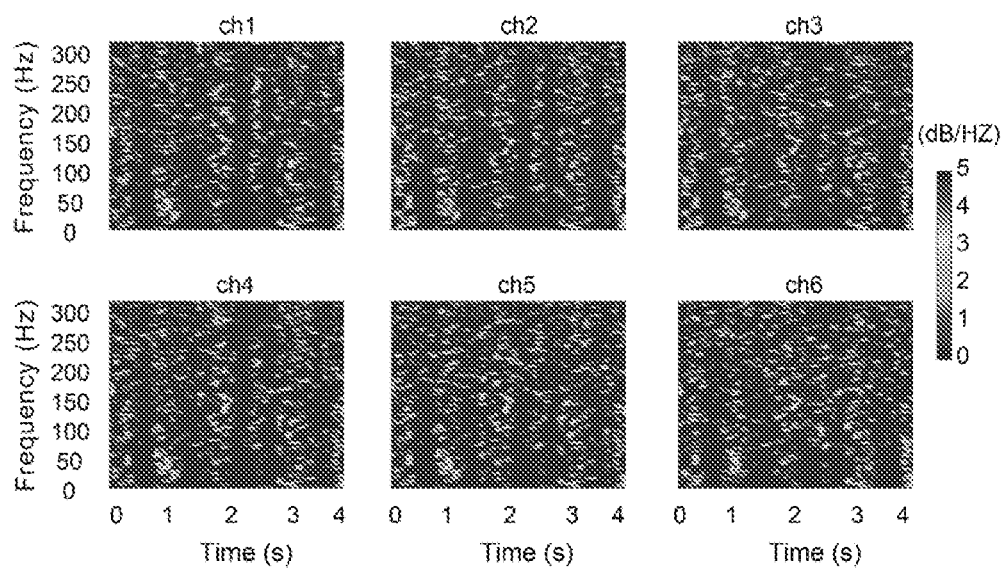
FIG. 14 depicts spectrograms of six electrocorticography (ECoG) channels during sensory-evoked potentials (SEPs) stimulation using a probe.

FIG. 14 depicts examples of spectrograms of six ECoG channels during sensory evoked potential (SEP) stimulation. Short time Fourier Transform was applied to the 256 ms section of each ECoG time series and smoothed by 200 ms overlapped windows to obtain this temporal-spectral representation of ECoG data.

Table 1 shows a summary of charge injection limits ($Q_{inj}$), charge storage capacity (CSC), and potential limits of electrodes including various materials, including carbon nanotube (CNT) pillars, carbon nanotubes by chemical vapor deposition (CNT-CVD), porous graphene, polyethylenedioxythiophene (PEDOT) carbon nanotubes (PEDOT-CNT), polypyrrole carbon nanotube composites (PPY-CNT), PEDOT, iridium oxide (IrOx), platinum (Pt), and glassy carbon. As shown in Table 1, with respect to CSC, glassy carbon electrodes may outperform electrodes made from other materials, including, for example, porous graphene, iridium oxide (IrOx), and platinum (Pt), among other materials. With respect to Qinj limit, glassy carbon electrodes may outperform electrodes made from other materials, including, for example, carbon nanotube pillars and platinum, among other materials. With respect to potential limit, glassy carbon electrodes may outperform electrodes made from, for example, polypyrrole-carbon nanotube composites (PPY-CNT), iridium oxide (IrOx), and platinum (Pt), among other materials.

TABLE 1

Summary of Charge Injection Limits (Qinj), Charge Storage Capacity (CSC) and Potential Limits of Microelectrode Materials

| Material | Coating | CSC (mC/cm$^2$) | Qinj limit (mC/cm$^2$) | Potential limit (V vs. Ag/AgCl) | Mechanism |
|---|---|---|---|---|---|
| CNT pillars | no | — | 1-1.6 | −1.5-1 | capacitive |
| CNT CVD | no | 70.8 ± 1.1 at 100 mV/s | 4 | −1-1.15 | capacitive |
| Porous Graphene | no | 50 at 100 mV/s | 3.2 | −1.3-0.8 | capacitive |
| PEDOT-CNT | yes | 40.4 ± 64.8, 158.7 ± 8.1, 540.7 ± 70.3 at 100 mV/s | 2.5-7 | −1-0.8 | pseudocapacitive |
| PPY-CNT | yes | 212.3 ± 23.9 | 7 | −0.9-+0.6 | pseudocapacitive |
| PEDOT | yes | 75.6 ± 5.4, 893.5 ± 137.8 at 100 mV/s | 2.3-15 | −0.8-+0.6 | pseudocapacitive |
| IrOx | yes | 28.8 ± 0.3 at 50 mV/s | 0.9-3.3 | −0.8-+0.6 | faradaic |
| Pt | no | 0.5 ± 0.1, 8.6 ± 3.5 | 0.05-0.15 | −0.8-+0.6 | pseudocapacitive |
| glassy carbon (Current) | no | 61.4 ± 6.9 | 3.0 | −0.9-+1.3 | capacitive |

Table 2 shows a summary of detection limits and sensitivity to dopamine detection for various electrode materials. With respect to detection limit, glassy carbon electrodes may outperform electrodes made from any of the other materials shown in Table 2.

TABLE 2

Summary of Detection Limits and Sensitivity to Dopamine Detection for various electrode materials.

| Material | Detection Limit | Sensitivity at 1 μM DA |
|---|---|---|
| CNT yarn electrodes | 25 ± 2 nM | — |
| Laser treated CNT yarn electrodes | 13 ± 2 nM | — |
| PEDOT/graphene oxide modified CF | 85 ± 9 nM | ca. 50 nA/μm$^2$ |
| CF | 19 ± 4, 218 ± 20 nM | — |

TABLE 2-continued

Summary of Detection Limits and Sensitivity to Dopamine Detection for various electrode materials.

| Material | Detection Limit | Sensitivity at 1 μM DA |
| --- | --- | --- |
| Self-assembled SWCNT forests | 17 ± 3 nM at 10 Hz, 65 ± 7 nM at 90 Hz | 184 ± 19 pA/μm$^2$ |
| CNT-Nb | 11 ± 3 nM | 197 ± 16 pA/μm$^2$ |
| glassy carbon (Current) | 10 nM | 450 ± 30 pA/μm$^2$ |

Figure 15:
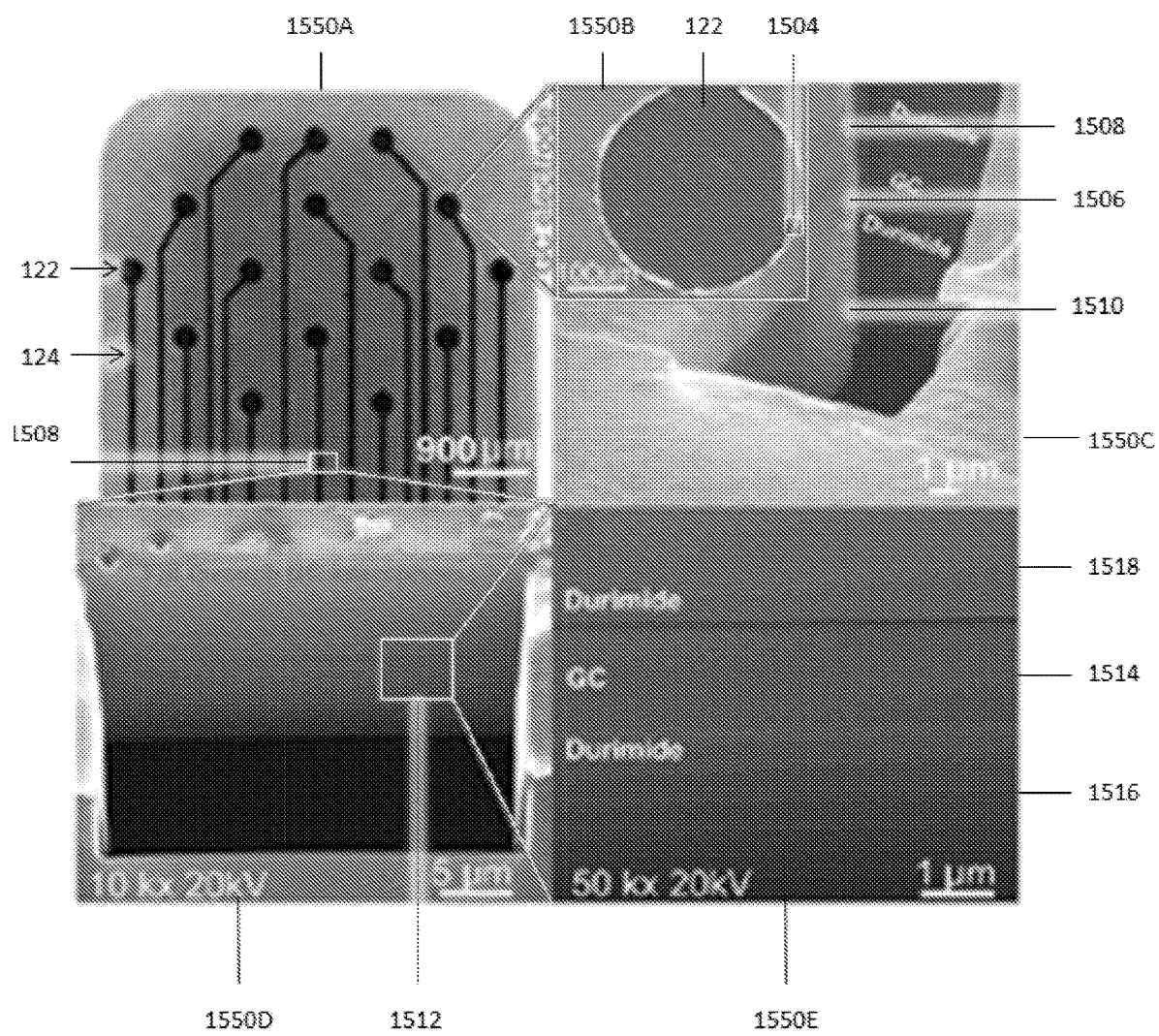
FIG. 15 depicts optical and scanning electron microscope images of a 15-channel probe.

FIG. 15 at 1550A depicts a 15-channel probe including the glassy carbon layer, in accordance with some example embodiments. Electrode 122 and interconnect regions 124 are visible on the probe at 1550A. This probe may be suitable for certain applications, including, for example ECoG. FIG. 15 at 1550B depicts a magnified scanning electron microscope image of a single electrode 122 in the 15-channel probe. An image of focused ion beam (FIB) cross-section appears in FIG. 15 at 1550C. The image at 1550C was taken of region 1504 at 1550B. The image at 1550C depicts the integration of the glassy carbon layer 1506 and the insulating layers 1508 and 1510. FIG. 15 at 1550D depicts an expanded view of a FIB cross-section taken of a glassy carbon interconnect region. The expanded view at 1550D was taken at region 1508 in the image at 1550A. FIG. 15 at 1550E shows a high-resolution (50,000×) FIB image of a cross-section taken through the glassy carbon interconnect region. The image at 1550E was taken at region 1512 at 1550D. The image at 1550E depicts the integration of the glassy carbon layer 1514 and the insulating layers 1516 and 1518 in the cross section of the interconnect region.

As shown in FIG. 15 at 1550A, the glassy carbon layer, including electrode 122, trace 124, and bump pad regions 126, are sharp and well-defined after microfabrication as disclosed herein. Both the first and second insulation layers appear structurally robust. As can be seen at 1550C and 1550E, FIB characterizations of glassy carbon/insulating layers at the electrode and interconnect regions demonstrate that the first and second insulation layers have an almost seamless interface with glassy carbon suggesting a strong bond between glassy carbon and polymer layers. This smooth and seamless interface is an important requirement for a tight integration and composite action between glassy carbon and the polymer layers.

Figure 16:
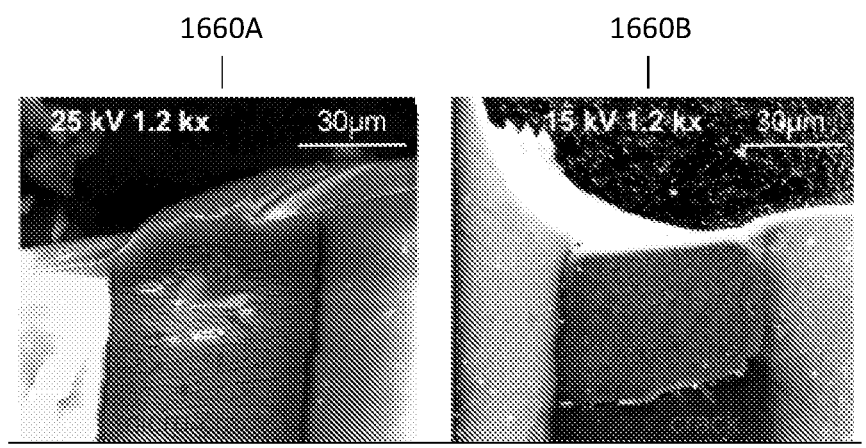
FIG. 16 depicts scanning electron microscope images following further mechanical testing of a probe.

FIG. 16 depicts failure planes at maximum load carrying capacity following mechanical testing of probes, as disclosed herein, as well as thin-film metal (Pt) probes. FIG. 16 at 1660A. depicts a scanning electron microscope (SEM) image highlighting failure plane in sample probes with metal traces where numerous micro-cracks were developed prior to and at time of failure. FIG. 16 at 1160B depicts a SEM image of failure plane in an probe as described herein. Apart from the failure plane, a single crack is observed at failure while the rest of glassy carbon trace remains intact. This micro-crack extends through the width of the specimen consistent with cracks that form during the failure of homogeneous materials. Load-deflection curves under a tensile load are reported along with calculated modulus.

For comparison purposes, tensile load tests were carried out on sample probes with thin-film metal (Pt) electrodes. The load carrying capacity for both types of probes was directly obtained from the load-deflection curves and the resulting failure planes in transverse direction were further investigated using SEM. The probes described herein failed at a tensile load of about 12 N at 1 mm extension with clearly defined elastic and plastic regions observed in the load-deflection curves. On the other hand, sample probes microfabricated with thin-film metal (Pt) electrodes and traces failed at an ultimate tensile load of 5 N at 0.7 mm extension. For both thin-film metal and glassy carbon traces, the failure plane as shown at 1660A-B passes through the traces with no jagged discontinuity, suggesting a strong bond between Durimide and the respective metal or glassy carbon layer. The Young's Modulus of the composite structure with glassy carbon electrodes and traces was calculated to be about 2.65 GPa whereas it was about 2.59 GPa for probes with Pt electrodes and traces. The modulus of probes was slightly higher than that of plain Durimide (2.5 GPa) suggesting a strong composite action between glassy carbon and polyimide. Optical observation revealed several micro-cracks in the thin-film metal traces near the failure plane (1660A), whereas only a single additional crack was seen in the otherwise intact glassy carbon trace 1660B), indicating different failure modes in the two types of probes. The extent of micro cracks in the thin-film metal electrodes suggests that they were progressively produced during loading resulting in earlier onset of electrical connection failure. For probes, failure in the traces under tensile load occurred at higher load levels preceding plastic failure as compared to other probes. Stiffness of probes in compression was determined through the Euler buckling load: Pcr=p$^2$EI/(KL)$^2$, where E=Young's modulus, I=area moment of inertia (500 mm width and 50 mm depth), K=effective length factor (usually 1) and L=length of probe. For the intracortical penetrating probes reported here, Pcr=2.13 mN, which is substantially higher than about 1.5 mN force required to penetrate the cerebral cortex of a rat.

Figure 17:
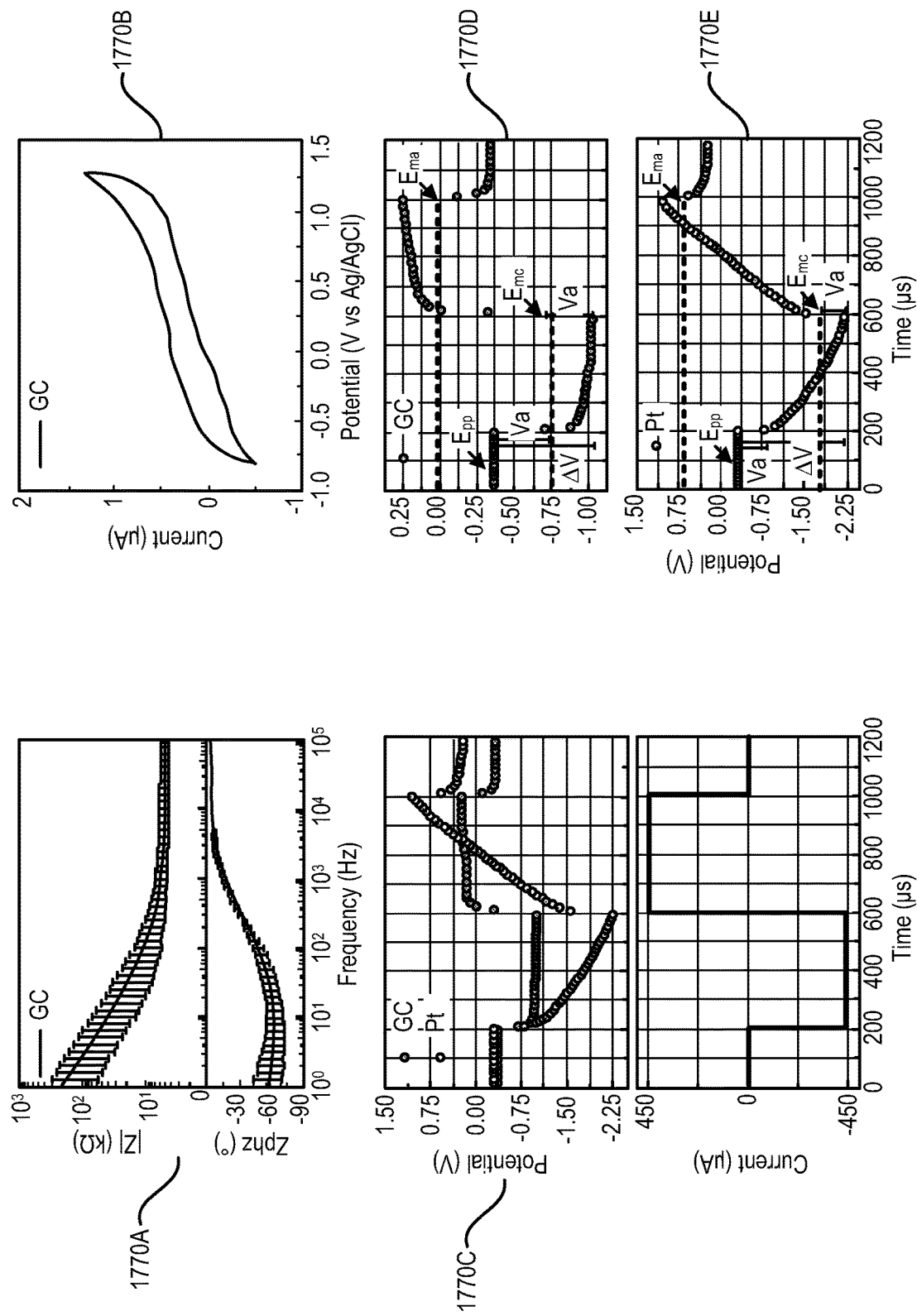
FIG. 17 depicts examples of results of electrochemical characterization tests a probe.

FIG. 17 depicts electrochemical characterization of the probe having the glassy carbon layer described herein. FIG. 17 at 1770A depicts an electrochemical impedance spectroscopy (EIS) plot (mean and standard deviation, n=10). FIG. 17 at 1770B depicts representative cyclic voltammogram. FIG. 17 at 1770C depicts a comparison of the voltage transient of glassy carbon versus Pt electrodes in response to a biphasic, symmetric 450 μA current pulses. FIG. 17 at 1770D depicts a voltage transient response of glassy carbon electrodes. FIG. 17 at 1770D depicts voltage transient response of Pt electrodes. Both plots show the components that contribute to the voltage transients (for example, $V_a$, $E_{ipp}$, $E_{mc}$ and $E_{ma}$). $E_{ipp}$ is the inter-pulse potential. $V_a$ is defined as the near-instantaneous voltage change at either the onset of the current pulse or immediately after the current pulse is terminated. It is associated with the Ohmic electrolyte resistance and overpotential terms. Maximum positive polarization $E_{ma}=V_{max,pos}-V_a$ whereas the maximum negative polarization $E_{mc}=V_{max,neg}-V_a$. The values of $E_{mc}$ and $E_{ma}$ for glassy carbon and Pt probes are (−0.75 V, 0 V) and (−1.75 V, 0.75 V) respectively, indicating a lower overpotential and lower-threshold for electrochemical kinetics of glassy carbon electrodes.

As shown in FIG. 17 at 1770A, impedance values at 10 Hz, 100 Hz and 1 kHz are (42.5±27.6) kΩ, (10.7±4.9) kΩ and (5.8±1.2) kΩ, respectively (mean and standard deviation, n=10). These indicate an excellent range for micro-ECoG recording applications. The corresponding EIS plots are reported at 1770A. As the phase plot at 1770A shows, impedances at frequencies higher than 4 kHz are dominated by almost exclusively a resistive component. The results of cyclic voltammetry of glassy carbon electrodes at 1770B demonstrate an approximately rectangular shape, characteristic of electrodes exhibiting a predominantly double-layer capacitance. This is consistent with the behavior of pure carbon materials, indicating that no faradaic reactions occur during the charging and discharging process. CSC, calculated as the time-integral of an entire CV cycle between the water oxidation and reduction potential limits, is 61.4±6.9 mC/cm2 (mean and standard deviation, n=10).

This capacitive charge injection mechanism is also confirmed by the voltage transient shape (FIG. 17 at 1770C) illustrating the comparison of voltage transients between glassy carbon and Pt electrodes with the same dimension of 300 μm diameter and comparable impedance. Traces are in response to a biphasic, symmetric current pulse of 450 μA amplitude and 400 msec of half-phase period. Due to the capacitive charge injection mechanism of glassy carbon electrodes, the amplitude of voltage transient for the same current level applied to both types of probes is much less in glassy carbon electrodes, producing maximum negative voltage ($V_{max,neg}$) of −1.03 V and maximum positive voltage ($V_{max,pos}$) of 0.25 V. These correspond to $E_{ma}$ (most negative polarization voltage) across electrode-electrolyte interface of −0.75 V and $E_{ma}$ (most positive polarization voltage) close to 0 V. These values are safely within the maximum potential limits of water reduction and oxidation for glassy carbon electrodes (for example, −0.9 to 1.3 V; 1770B). In contrast, for Pt electrodes, the corresponding $V_{max,neg}$, $E_{mc}$, $V_{max,pos}$ and $E_{ma}$ values are −2.25 V, −1.75 V, 1.07 V and 0.7 V, respectively. These values are substantially outside the maximum potentials corresponding to the water window of Pt at −0.6 V to 0.8 V. Note that the maximum negative potential excursion ($E_{mc}$) is calculated by subtracting the access voltage ($V_a$) associated with the Ohmic electrolyte resistance and overpotential terms from the maximum negative voltage in the transient (for example, $E_{mc}=V_{max,neg}-V_a$ and $E_{ma}=V_{max,pos}-V_a$). $V_a$ may be defined as the near-instantaneous voltage change at either the onset of the current pulse or immediately after the current pulse is terminated. In this condition, $V_a$ is 0.36 V for glassy carbon and 0.48 V for Pt (33% higher for Pt), suggesting a substantially lower overpotential to be overcome in glassy carbon electrodes (FIG. 1770C-D.) Table 3 summarizes these results.

TABLE 3

Summary of key parameters in voltage transients for glassy carbon and Pt electrodes

| Material | DV | Eipp | $V_a$ | $DE_p$ | Emc | Ema | Vmax, neg | Vmax, pos |
|---|---|---|---|---|---|---|---|---|
| glassy carbon | 0.72 | −0.36 | 0.36 | 0.36 | −0.75 | 0.05 | −1.03 | 0.25 |
| Pt | 1.88 | −0.31 | 0.48 | 1.4 | −1.75 | 0.71 | −2.25 | 1.07 |

Figure 18:
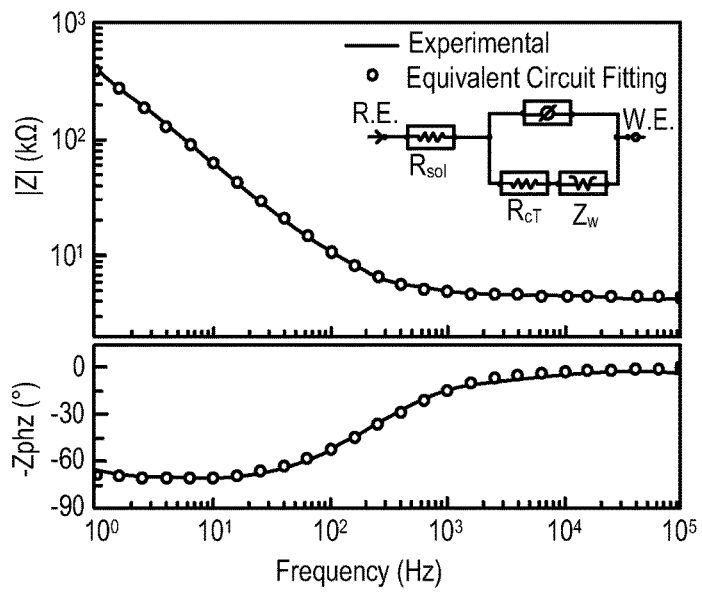
FIG. 18 depicts an equivalent circuit model of a probe, such as a electrode.

FIG. 18 depicts an equivalent circuit for glassy carbon electrodes based on a modified Randles model. Representative electrochemical impedance spectroscopy (EIS) impedance spectra for experimental data (solid line) and equivalent circuit fitting (circles) used for curve fitting are shown.

Further, to gain better understanding of the charge transfer properties of the glassy carbon electrodes, an equivalent circuit model was curve-fitted to the experimental EIS data. Representative EIS bode plots of the experimental data and curve-fitting of the most appropriate equivalent circuit model are reported in FIG. 18. The optimal model with the best fit is a modified Randles circuit that is composed of electrolyte resistance ($R_{sol}$) in series with a parallel combination of charge transfer resistance ($R_{ct}$), constant phase element ($Z_{CPE}$), and Warburg impedance ($Z_w$). The modified Randles equivalent circle selected here is consistent with results reported in the literature for capacitive electrodes. In this model, the constant phase element ZCPE is define as: $ZCPE=1/(j\omega)^\alpha Y_o$ where $Y_o$ represents the capacitance and $\alpha$ is a constant related to the angle of rotation in the complex plane compared to the purely capacitive behavior ($Y_o=1$ for a pure capacitor). The corresponding parameters obtained by fitting the experimental data to the model are: Rsol=4.4 kΩ, $Z_{CPE}$ with $Y_0=4.07e^{-11}$ S*$s^\alpha$ and $\alpha=0.87$, $Z_w=2.74^{-11}$ S*$S^{1/2}$, and Rct=3.34 kΩ.

Figure 19:
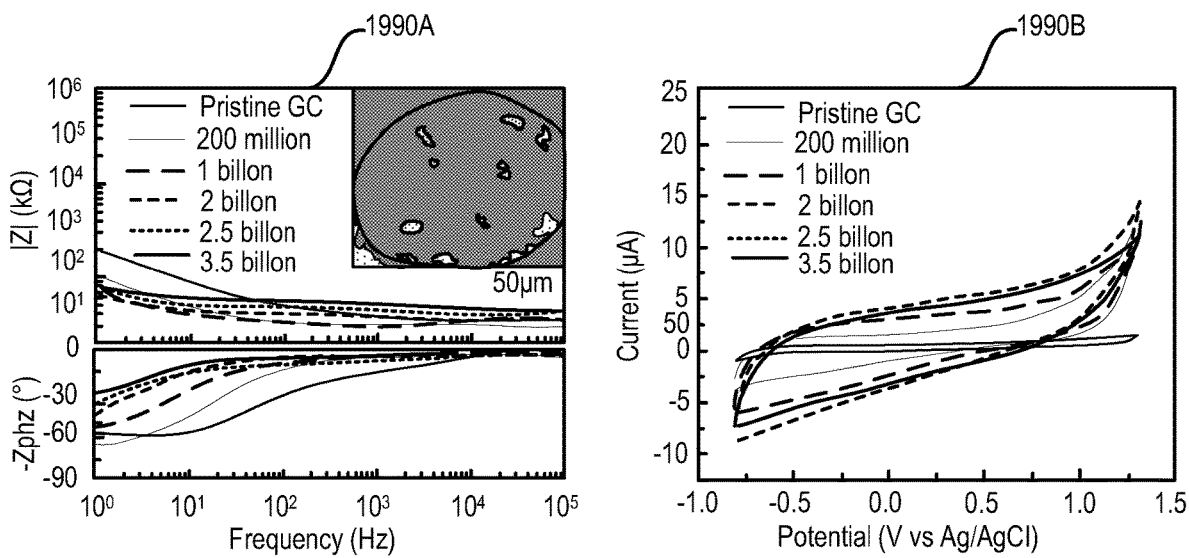
FIG. 19 depicts example of the results of accelerated aging tests on a probe.

FIG. 19 depicts the effect of accelerated aging on glassy carbon electrodes through bi-phasic pulsing in phosphate buffered saline (PBS) for 42 days (1000 hours). FIG. 19 at 1990A depicts the impedance spectra before and after 0.2, 1, 2, 2.5 and 3.5 billion cycles of stimulation pulses in PBS at 0.25 mC/cm2 charge density. The inset depicts an SEM image of a glassy carbon electrode after 3.5 billion cycles of pulses. FIG. 19 at 1990B depicts the corresponding cyclic voltammograms over a range of stimulation pulses.

Results from accelerated aging test with cycles of electrical pulse applied over period of 1000 hours are reported at 1990A-B. FIG. 19 summarizes EIS plots, CV cycles and voltage transients of glassy carbon electrodes before and after 0.2, 1, 2, 2.5 and 3.5 billion cycles of electrical stimulation pulses. Prior to pulsing, for example, the impedance value at 1 kHz was about 5.2 kΩ. After 2, 2.5 and 3.5 billion cycles of pulses, the impedance at 1 kHz was measured to be 5.75, 6.3, 8.8 kΩ, respectively. In general, a decrease in impedance at low frequency ranges was observed, with a shift of the low frequency pole and a corresponding increase in CSC. The CSC values increased from 45 mC/cm2 to 180 mC/cm2 after 0.2-3.5 billion cycles of pulsing. This increase in capacitance is predominantly due to continued surface activation that is very common in carbon electrodes. The corresponding CV cycles are reported in FIG. 19 at 1990B, exhibiting the expected rectangular shape of capacitive electrodes. Again, as CV diagrams demonstrate, there are no observable faradaic reactions occurring during charging and discharging processes.

As part of this accelerated aging test, pH value of about 7.55 was measured at several locations in the flow-cell, well within the buffer's initial pH of 7.4. This is expected due to the buffering action of the PBS solution. Moreover, these findings are consistent with pH levels predicted by transient FEA models, where pH near the electrode surface returned back to the initial conditions after each charge-balanced cycle.

Figure 20:
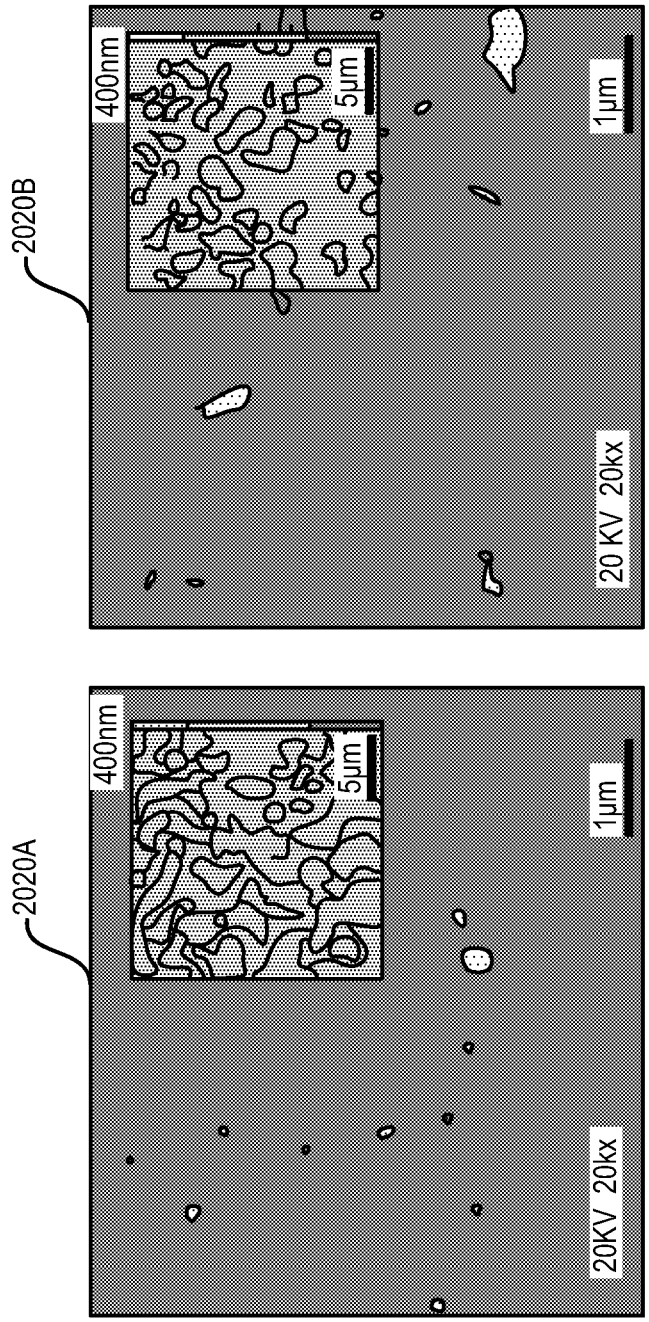
FIG. 20 depicts images of a probe before and after undergoing aging tests.

FIG. 20 depicts scanning electron microscope (SEM) and atomic force microscope (AFM) images of the surface of a glassy carbon electrode, as described herein. FIG. 20 at 2020A depicts the electrode before stimulation. The SEM and AFM inspections show that the mechanical integrity of the electrode was still intact after 3.5 billion cycles of biphasic 0.25 $mC/cm^2$ pulses in phosphate buffered saline (PBS) solution over a period of 42 days, as shown at 2020B. SEM images confirm that the insulating layers remained intact and well attached to glassy carbon electrodes at the end of this accelerated aging under electrical stimulation. The AFM images of the electrodes were taken of a 25 μm×25 μm area before and after aging to determine if there was any quantifiable and visible corrosion of the exposed electrodes. AFM morphology analysis indicated that, before stimulation, mean roughness of the electrode surface was 43.55±3.09 nm (n=4) while after stimulation, it was 44.00±6.69 nm (n=4). A corresponding t-test gave a non-significant difference (P value>0.05) between the mean roughness of the surfaces under the two conditions, confirming that there was no discernible corrosion after the aging process.

Figure 21:
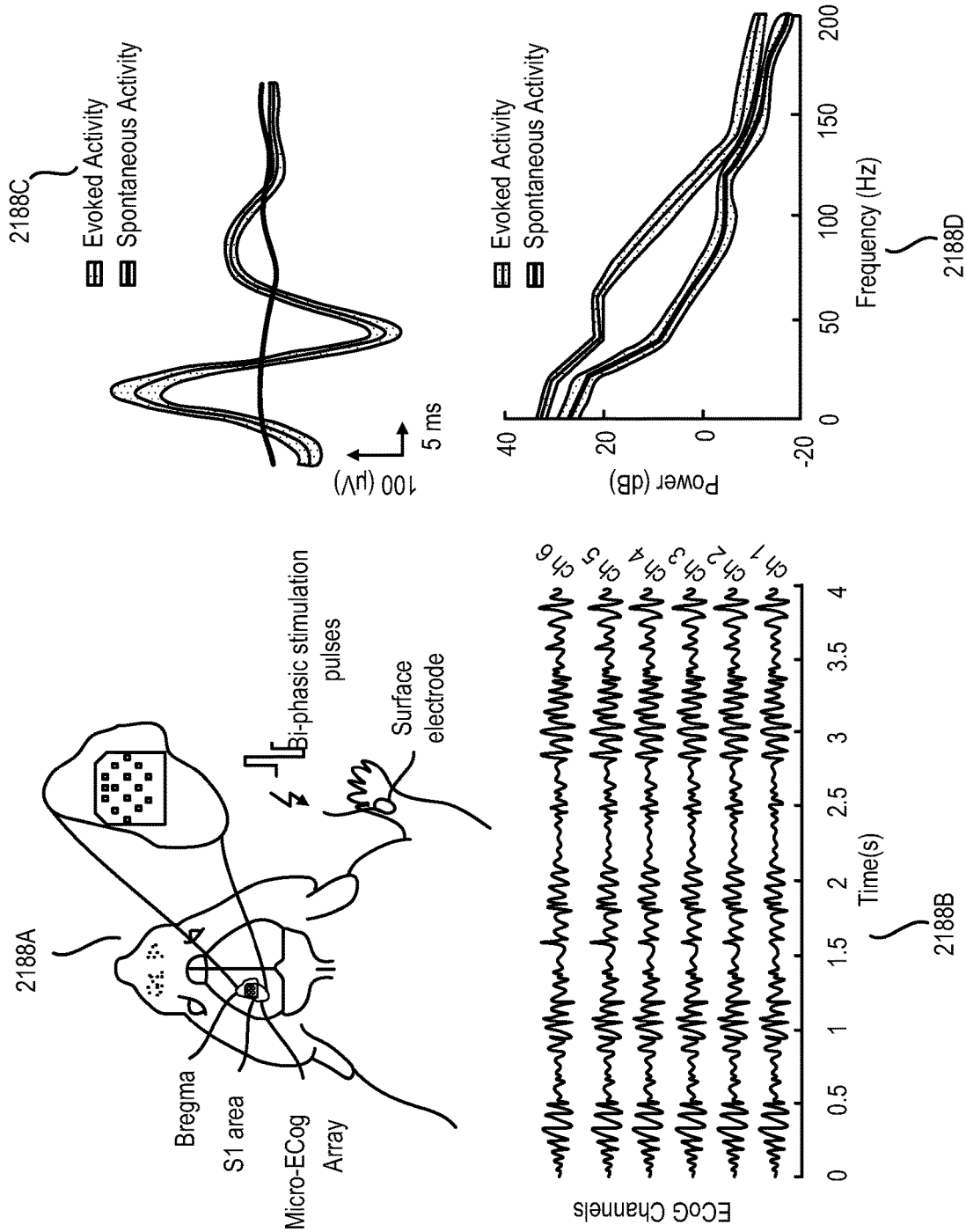
FIG. 21 depicts an example of test results from in-vivo testing of a probe.

FIG. 21 at 2188A depicts a schematic figure showing implantation site of a probe, as described herein, on the left forelimb sensory cortex of an anesthetized rat. Electrical stimulation was applied on the skin of the right wrist. 2188B depicts an example of raw ECoG data recorded using an probe implanted on the forelimb area of a rat sensory cortex. 2188C depicts an average sensory evoked potential (SEP) response related 5 to 55 ms after surface electrical stimulation of hand skin, with the average-spontaneous activity related to 65 to 115 ms after stimulation. 2188D depicts the power spectrum (mean±standard error) for sensory evoked response and spontaneous activities corresponding to the same signals shown in FIG. 21 at 2188C.

Sensory evoked potentials (SEPs) caused by the bi-phasic stimulation pulses on the right wrist were recorded via the ECoG aCG probe, as described herein, implanted on the left forelimb sensory cortex of an anesthetized rat. FIG. 21 at 2188A shows the craniotomy made targeting the left forelimb sensorimotor cortex where the probes were implanted. Plots of brain activities sampled from six channels of electrodes implanted in the sensory cortex four days after the implantation surgery are shown in FIG. 21 at 2188B. To verify the quality of brain recording using glassy carbon electrodes, the average-SEP of different channels were calculated in response to the surface electrical stimulation of hand area. FIG. 21 at 2188C shows a typical average-SEP (mean±standard error) of a single ECoG channel for 5 ms to 55 ms after stimulation onset, with average-spontaneous activity of the same ECoG channel for 65 ms to 115 ms after stimulation onset. The time frame between 5 ms to 55 ms was considered adequate to cover the entire SEP response, as all SEPs were observed in this time range. The large positive and negative response corresponding to 15 ms after stimulation onset demonstrates that the ECoG electrodes successfully recorded early response of sensory neurons in somatosensory cortex in the presence of background spontaneous activity.

FIG. 21 at 2188D shows the power spectrum of the same six channels. As can be seen, all of the electrodes recorded brain activities in physiological spectral range without interference from non-physiological noise such as power line noise. Further, Supplementary Figure S6 shows that the spectrograms representing brain signals could be recorded across different frequency bands using glassy carbon electrodes. In Table 4, the mean (±standard deviation) SNR value (16±6) and impedance of all ECoG channels are shown. Collectively, the in-vivo tests demonstrate that the ECoG microarray can successfully record multi-site, temporal and spectral brain information with high SNR.

TABLE 4

Average electrical recording SNR value and impedance of glassy carbon electrodes arrays implanted in the forelimb area of rat sensory cortex.

| SNR | In-vivo Impedance of | Impedance of |
|---|---|---|
| 16 ± 6 | 81 ± 16 | <0.1 |

Figure 22:
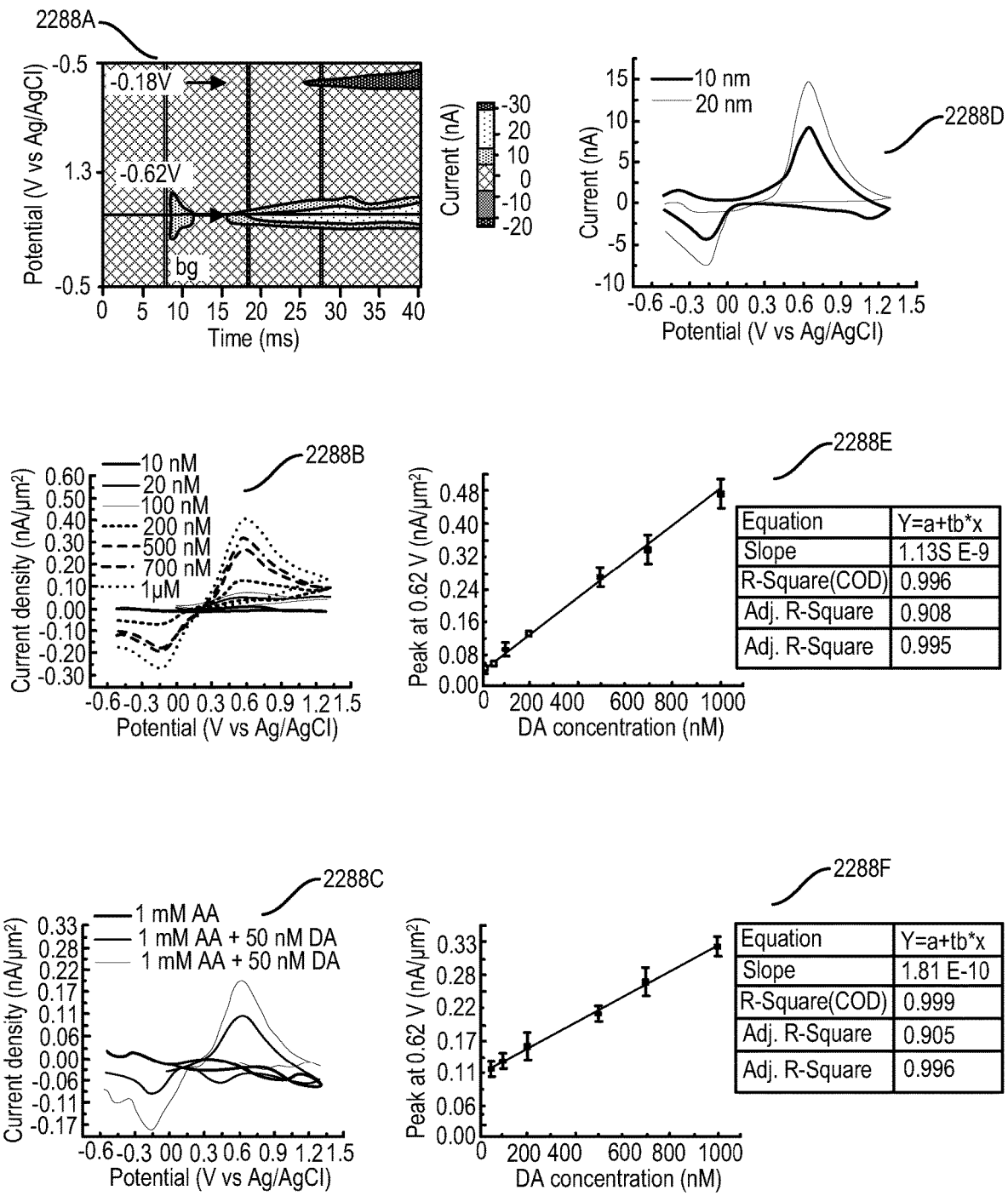
FIG. 22 depicts examples of test results from in-vitro testing of a probe.

FIG. 22 summarizes results obtained from a series of fast-scan cyclic voltammetry (FSCV) characterizations using penetrating glassy carbon probes with a net surface area of 500 $mm^2$. FIG. 22 at 2288A depicts an example of dopamine signals detected using a standard pyramidal FSCV waveform in which the applied voltage was ramped from the holding potential of −0.5 V to the switching potential of +1.3 V and then back to −0.5 V at 400 V/s scan-rate. In particular, the color plots show changes in current following the injection of 10 nM of dopamine (DA) at t=15 secs first and subsequently an additional 10 nM at t=25 sec in the base phosphate buffered saline (PBS) buffer. These changes in currents occurred at the known reduction and oxidation peaks of DA (i.e., −0.18 V and 0.62 V), as clearly shown in the background subtracted CVs for 10 nM and 20 nM dopamine given in FIG. 22 at 2288B. Further, to determine a calibration curve over a wider range of concentrations, additional sets of FSCV were carried out at 10, 20, 50, 100, 200, 500, 700 nM and 1 mM concentration of dopamine in PBS. As shown in FIG. 22 at 2288C, the background subtracted CVs corresponding to these range of concentrations demonstrate reduction and oxidation peaks at (−0.18 V) and (0.62 V). In addition, the calibration curve for these concentrations of dopamine varying from 10 nM to 1 mM follows a linear trend as reported in FIG. 22 at 2288D. This low detection limit of dopamine at 10 nM represents one of the lowest reported limits in the literature. Further, the capability of this platform for selective detection of dopamine in the presence of ascorbic acid (AA) was also investigated. Ascorbic acid typically occurs in much higher concentration than that of dopamine (100-1000 times) and strongly interferes with dopamine detection. Hence, the determination of dopamine with high selectivity and sensitivity in presence of ascorbic acid is desirable for diagnostic applications. Glassy carbon electrodes were able to detect 50 nM dopamine in the presence of 1 mM ascorbic acid with high resolution. Background subtracted CVs showing reduction (−0.2 V) and oxidation (0.6 V) peaks of 50 nM and 500 nM of dopamine in presence of 1 mM ascorbic acid in PBS are reported in FIG. 22 at 2288E. The corresponding calibration curve shows a linear trend (FIG. 22 at 2288F.) This capability uniquely underscores an additional strong asset of glassy carbon electrodes in neurotransmitter detection through FSCV, a capability that is not matched by thin-film metal or metal oxide electrodes.

Probes, as described herein, may allow long-term electrical stimulation with minimal or undetectable material corrosion of the electrode. Cross-section characterization through focused ion beam (FIB) and scanning electron microscope (SEM) imaging show a strong attachment enabled by hydroxyl and carbonyl covalent bonds between glassy carbon microstructures and between the first and second insulating layers. Extensive in-vivo and in-vitro tests have shown that probes may have a dopamine detection in the range of 10 nM. These probes in particular may offer an improved multi-modal platform for long-term applications of probe technology in both experimental and clinical neuroscience.

Brain stimulation applications may require electrodes capable of hundreds of millions of cycles of electrical stimulation pulses at clinically relevant charge densities, corresponding to probes that may be implanted for a very long period of time, for example, 3 to 5 years. Glassy carbon probes, according to example embodiments, may be able to deliver this level of performance with minimal or undetectable corrosion, minimal or undetectable tissue damage, and minimal or undetectable delamination of insulating layers. Probes implemented in accordance with example embodiments may thus enable the transition of probe technology from lab use to clinical use, including, for example, deep brain stimulation and spinal stimulation used for neuromodulation or induction of neuroplasticity.

These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. For example, the instructions for manufacturing the hybrid system may be implemented in program code and taped out to enable manufacturing at other locations. The computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. A probe comprising:
   a first insulating layer; and
   a glassy carbon layer on at least a portion of the first insulating layer;
   wherein the glass carbon layer provides one or more channels to enable acquisition of one or more signals, each of the one or more channels comprising a microstructure,
   wherein the microstructure comprises a bump pad, an interconnect defining a trace, and an electrode,
   wherein an upper surface of the bump pad, an upper surface of the interconnect, and an upper surface of the electrode are disposed on a same plane that forms a surface of the glass carbon layer, and
   wherein the glassy carbon layer including the bump pad, the interconnect, and the electrode are composed of glassy carbon.

2. The probe of claim 1 further comprising:
   a second insulating layer on at least a portion of the glassy carbon layer, the second layer is layered over the interconnect, wherein the second insulating layer is not layered over the bump pad and the electrode.

3. The probe of claim 1, wherein the one or more channels comprises a plurality of channels to form an array of electrodes, each of the plurality of channels comprises a respective microstructure.

4. The probe of claim 1, wherein the bump pad is configured as an interface to enable the probe to be coupled to at least an external device.

5. The probe of claim 1, wherein the microstructure comprising the bump pad, the interconnect, and the electrode are formed from a same layer of precursor material during pyrolysis.

6. The probe of claim 3, wherein the array of electrodes is configured as a microarray.

7. The probe of claim 1, wherein the electrode is sized between 1 square nanometer and 1 square meter to enable the electrode to make contact with at least a portion of a patient or test subject.

8. The probe of claim 1 further comprising:
   a device coupled to the probe, the device delivering and/or receiving, via at least the microstructure, the one or more signals to the probe.

9. The probe of claim 8, wherein the device is configured to provide electrocorticography, electroencephalography, neural stimulation, or electromyography.

10. The probe of claim 1, wherein the glassy carbon is formed from patterned pyrolysed carbon.

11. The probe of claim 1, wherein the glassy carbon layer is positioned between the first insulating layer and a second insulating layer.

12. The probe of claim 2, wherein the first insulating layer is positioned on a first side of the interconnect, and wherein the second insulating layer is layered over a second side of the interconnect opposite the first side.

13. The probe of claim 1, wherein each of the bump pad, the interconnect, and the electrode does not include metal.

* * * * *